(12) United States Patent
Daum

(10) Patent No.: US 6,238,355 B1
(45) Date of Patent: May 29, 2001

(54) TUMORTHERAPY DEVICE AND METHOD

(75) Inventor: Wolfgang Daum, Schwerin (DE)

(73) Assignee: Daum GmbH, Schwerin (DE)

(*) Notice: Subject to any disclaimer, the term of this patent is extended or adjusted under 35 U.S.C. 154(b) by 0 days.

(21) Appl. No.: 09/032,723

(22) Filed: Feb. 27, 1998

(30) Foreign Application Priority Data

Feb. 16, 1998 (DE) .............................................. 198 06 693

(51) Int. Cl.[7] ...................................................... A61B 5/00
(52) U.S. Cl. .................................................................. 600/567
(58) Field of Search ............................ 600/562, 564–568; 604/264

(56) References Cited

U.S. PATENT DOCUMENTS

| | | | |
|---|---|---|---|
| 5,197,484 | * 3/1993 | Kornberg et al. | 600/567 |
| 5,249,583 | * 10/1993 | Mallaby | 600/567 |
| 5,280,427 | * 1/1994 | Magnusson et al. | 600/567 |
| 5,830,219 | * 11/1998 | Bird et al. | 600/562 |

* cited by examiner

Primary Examiner—Max Hindenburg
(74) Attorney, Agent, or Firm—Altera Law Group, LLC

(57) ABSTRACT

The invention provides devices and methods for removing a consolidated mass, such as a tumor, from a dense tissue. In one embodiment, a device of the invention comprises a system of telescoping needles for separating or widening the dense tissue for exposure of the consolidated mass. In some embodiments, a device further comprises an arrangement for cutting out the mass. In another embodiment, the invention provides for obtaining a diagnostic biopsy of the consolidated mass prior to removal of the mass.

42 Claims, 22 Drawing Sheets

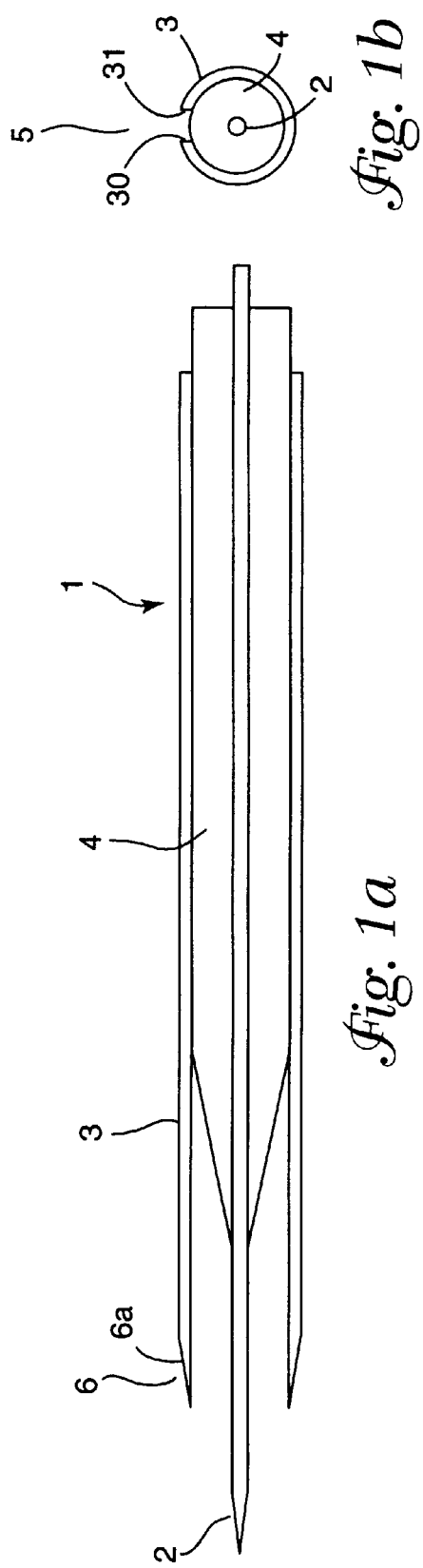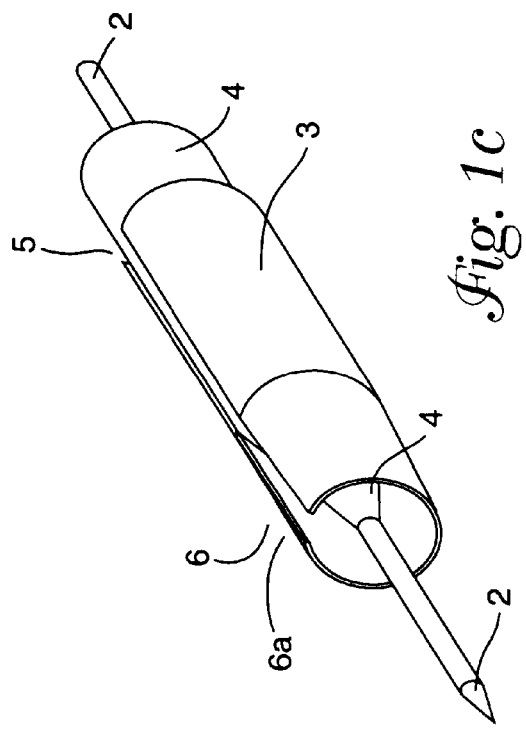

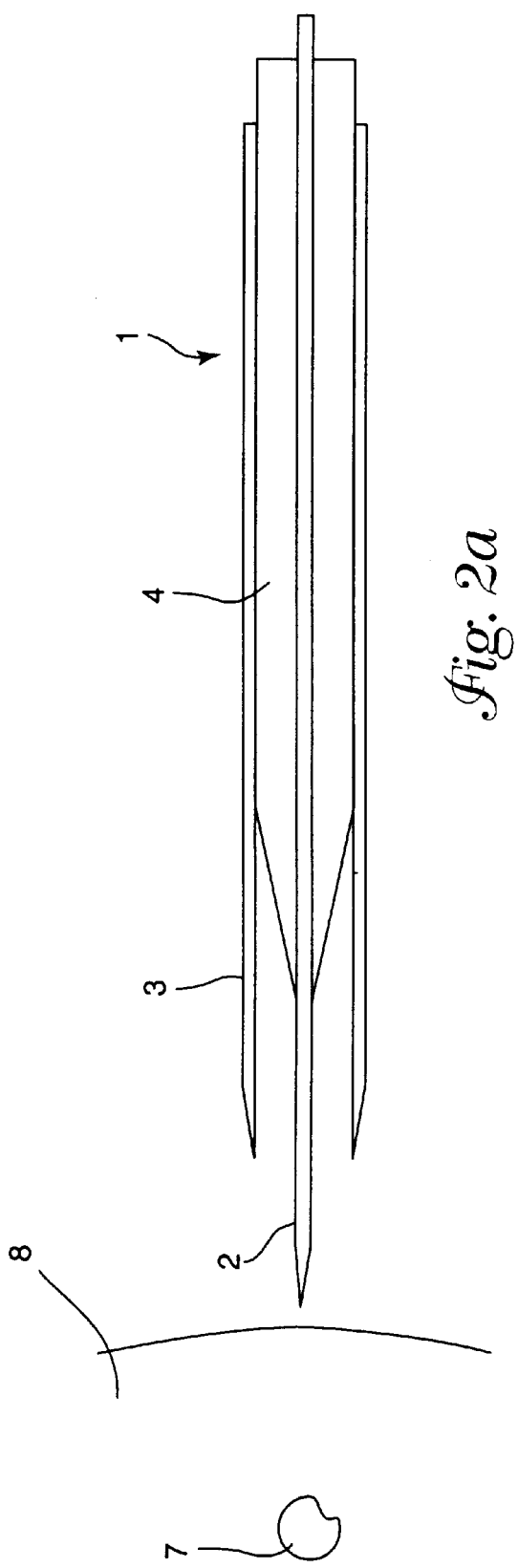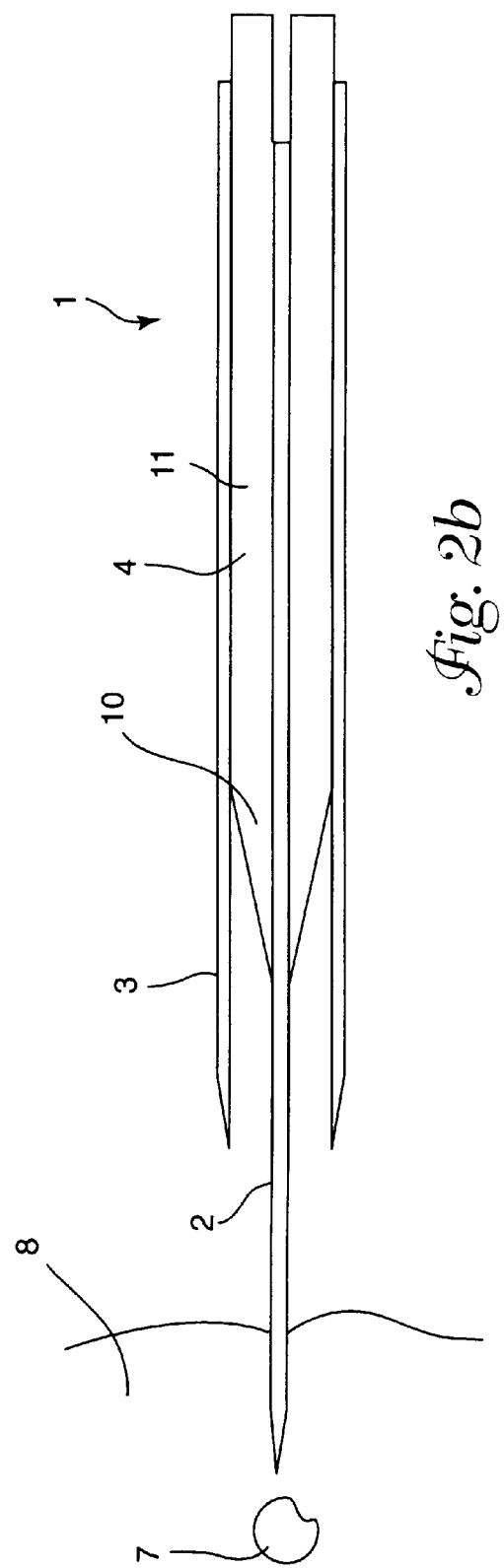

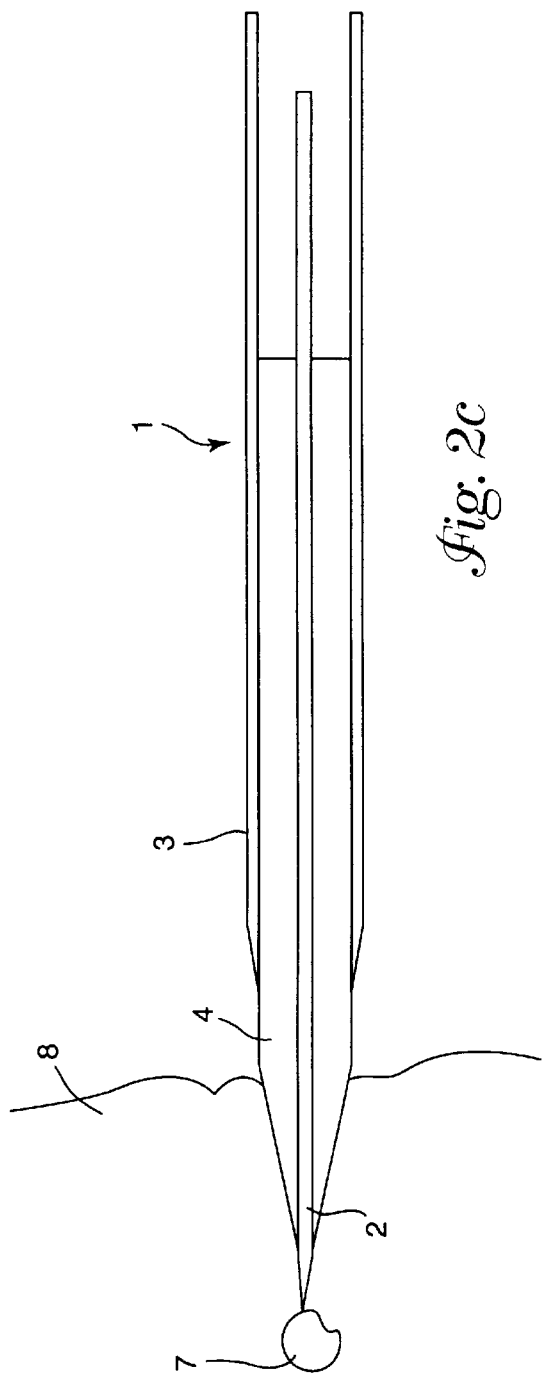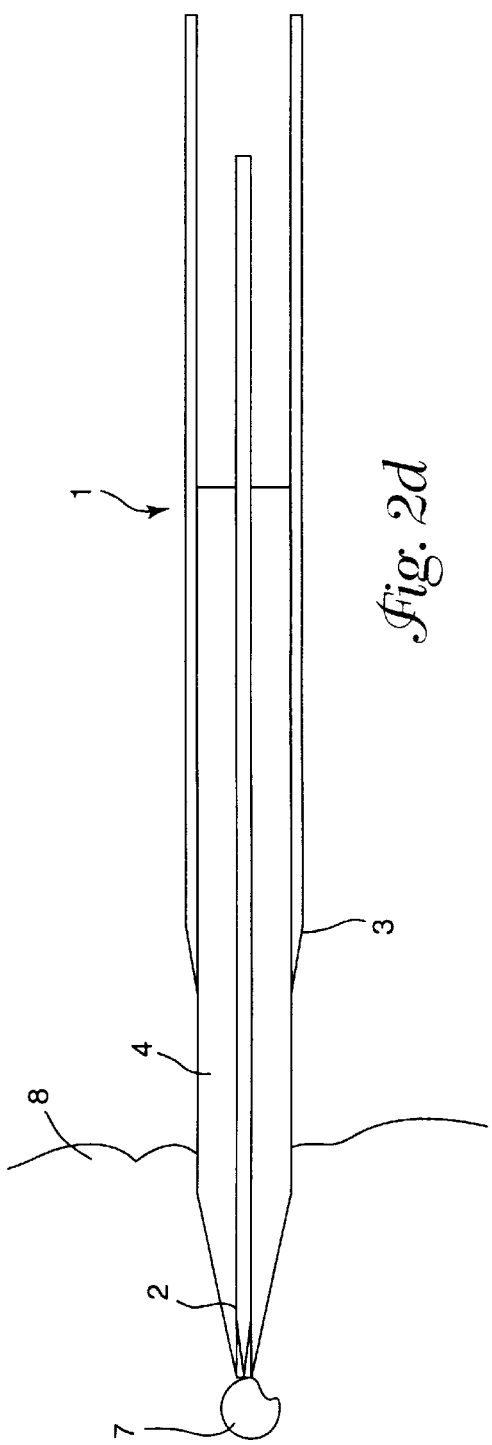

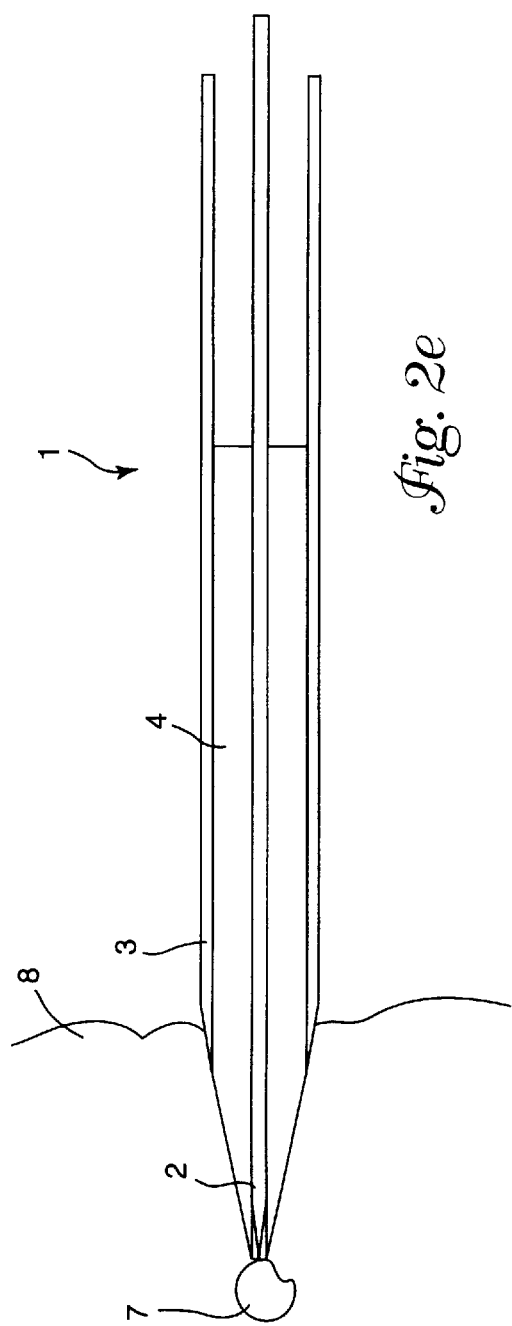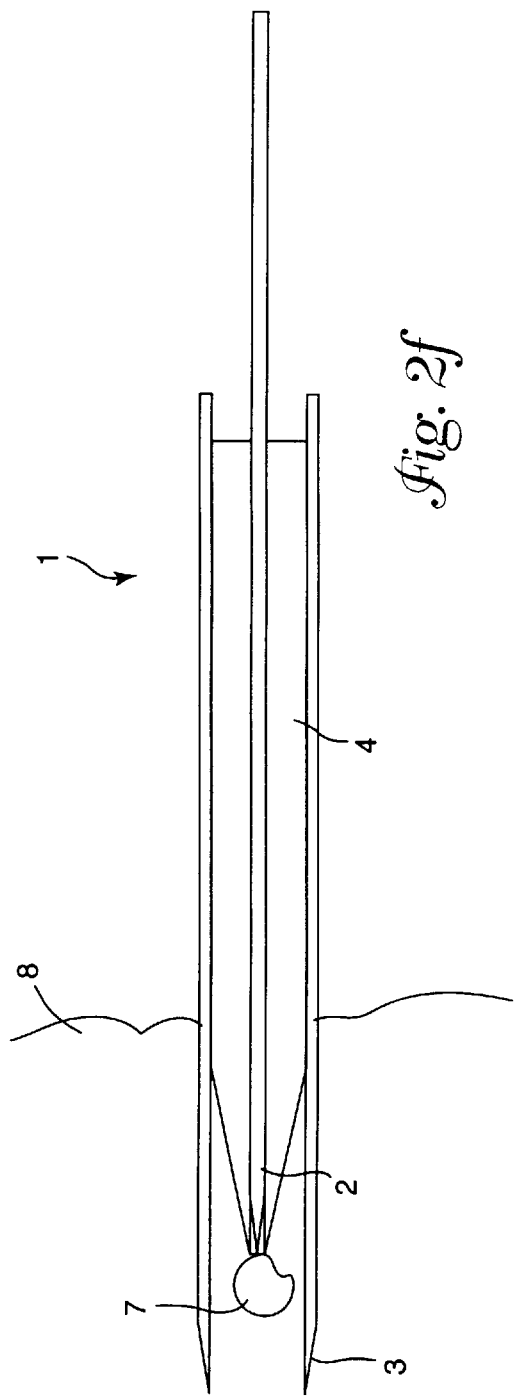

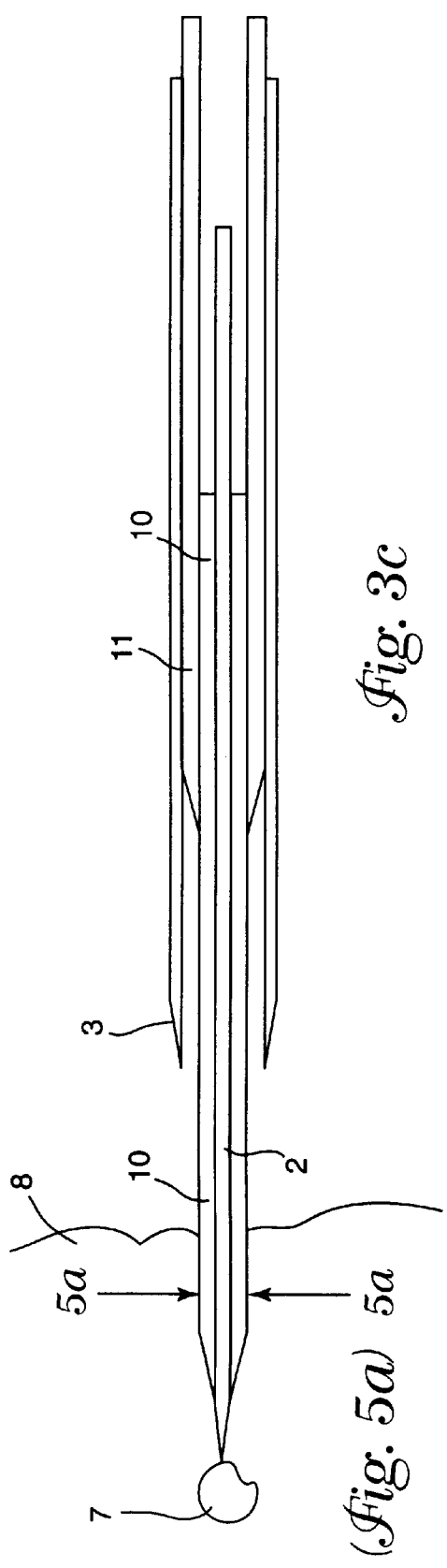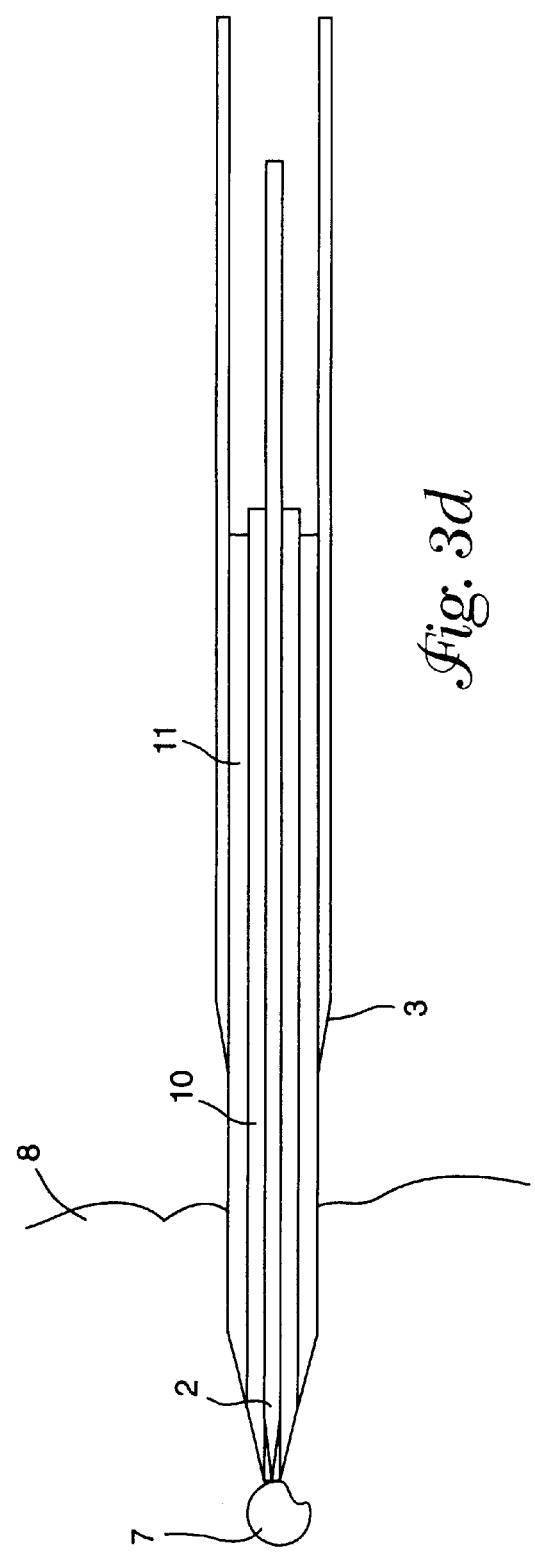

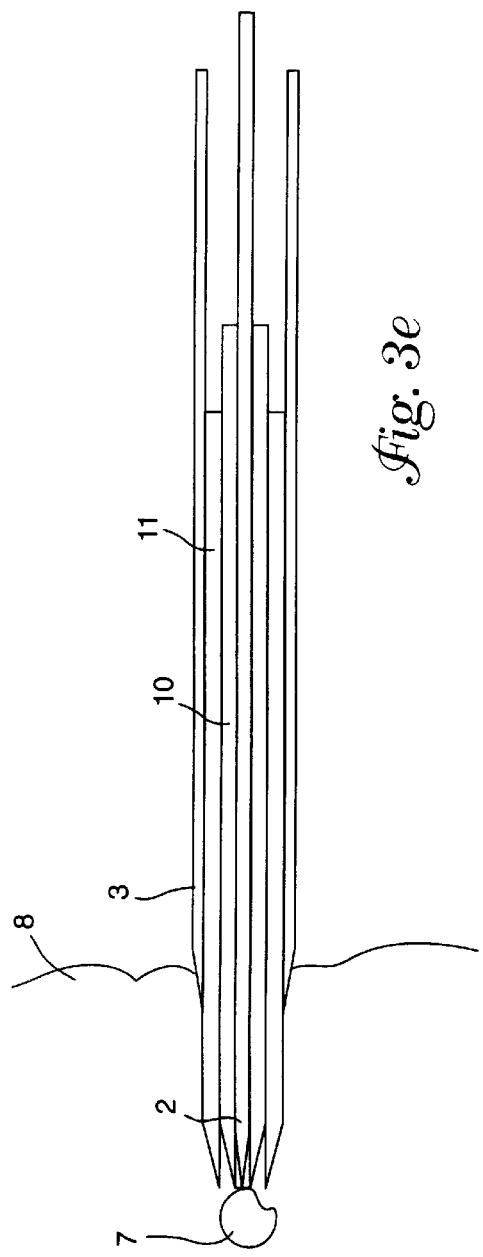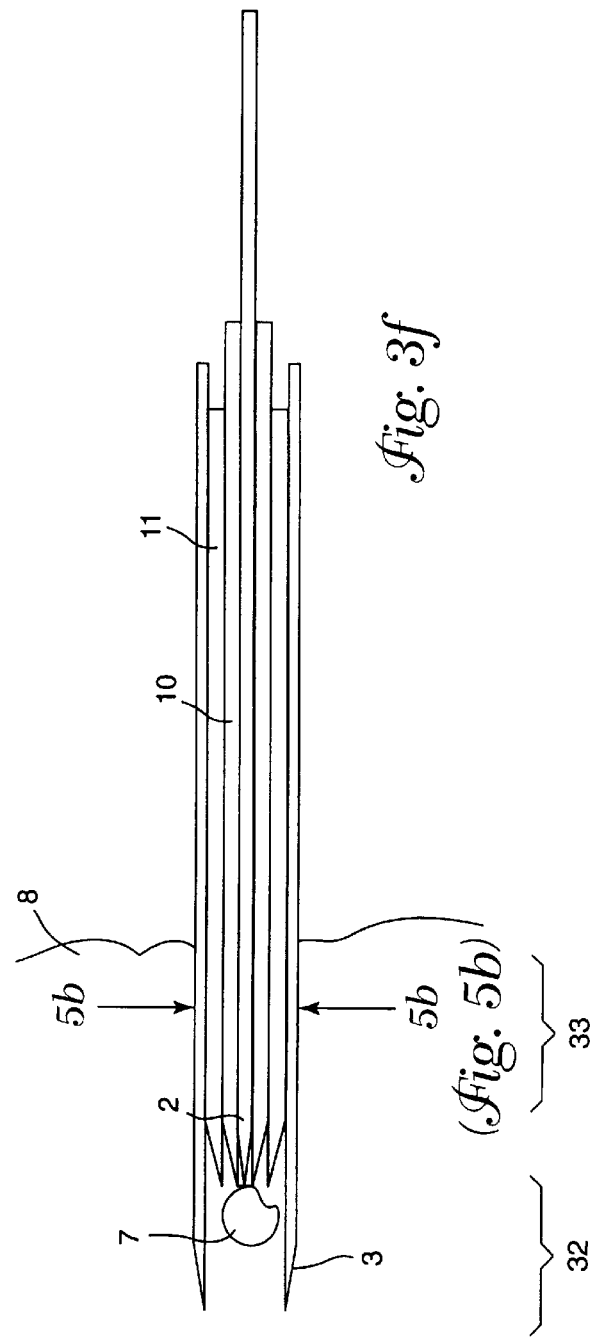

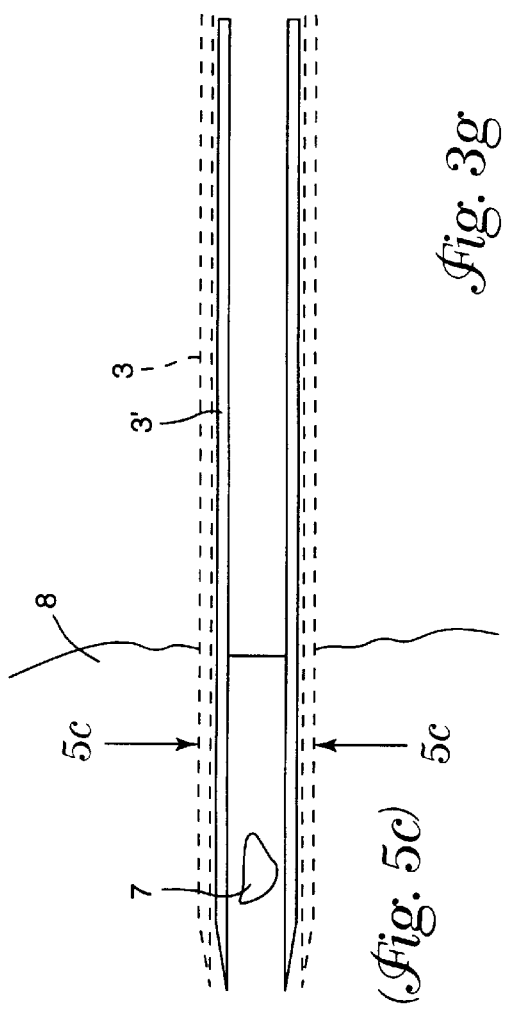
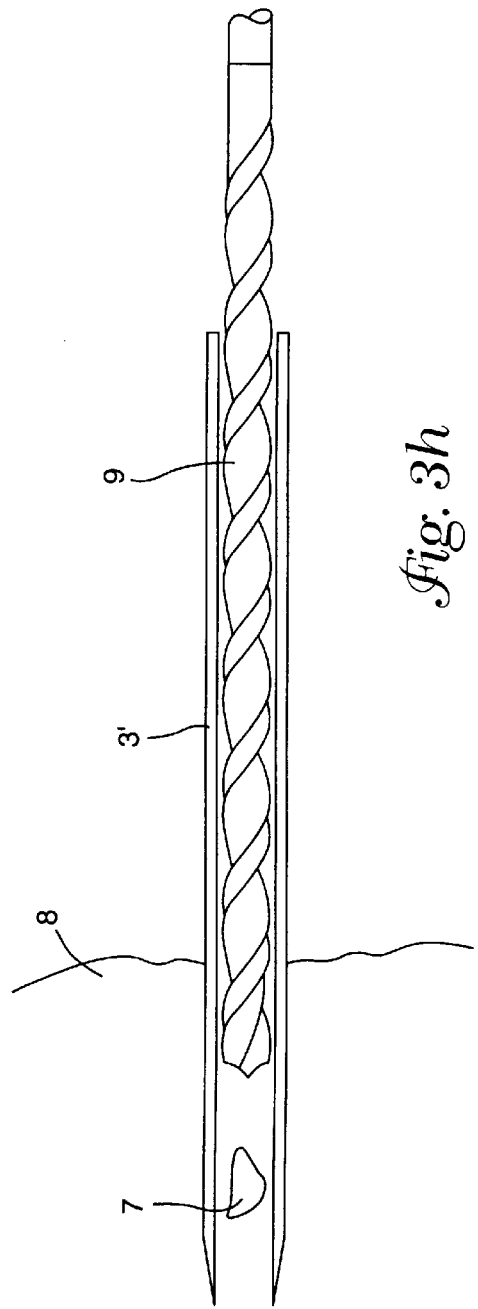

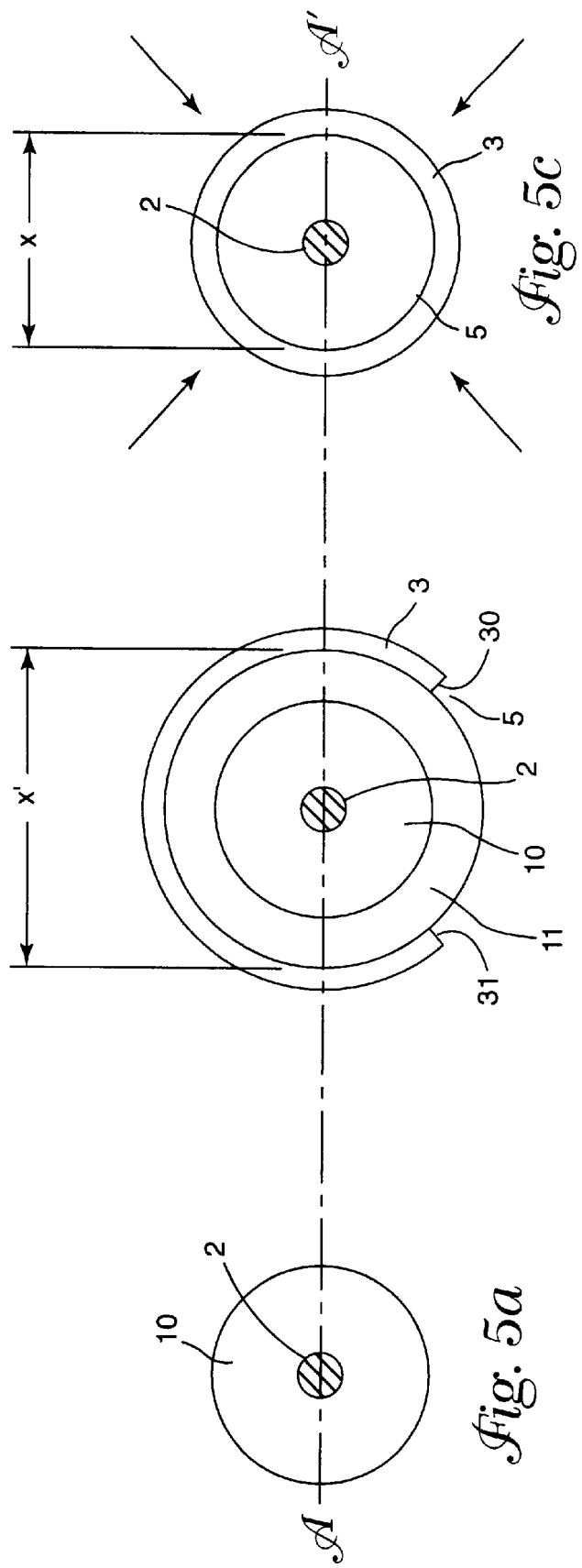

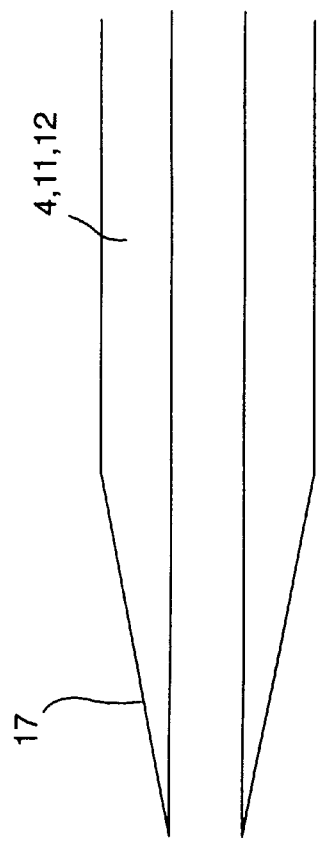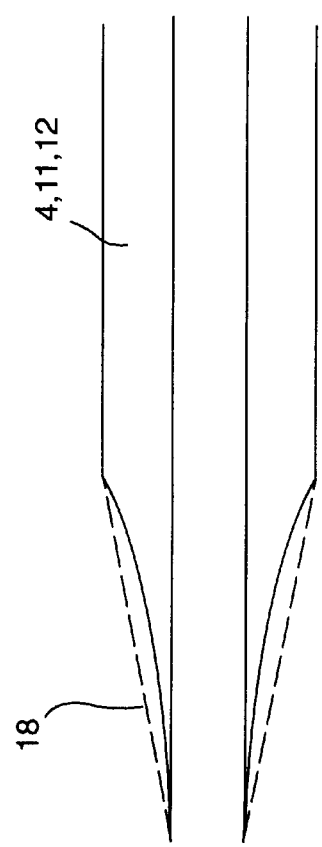

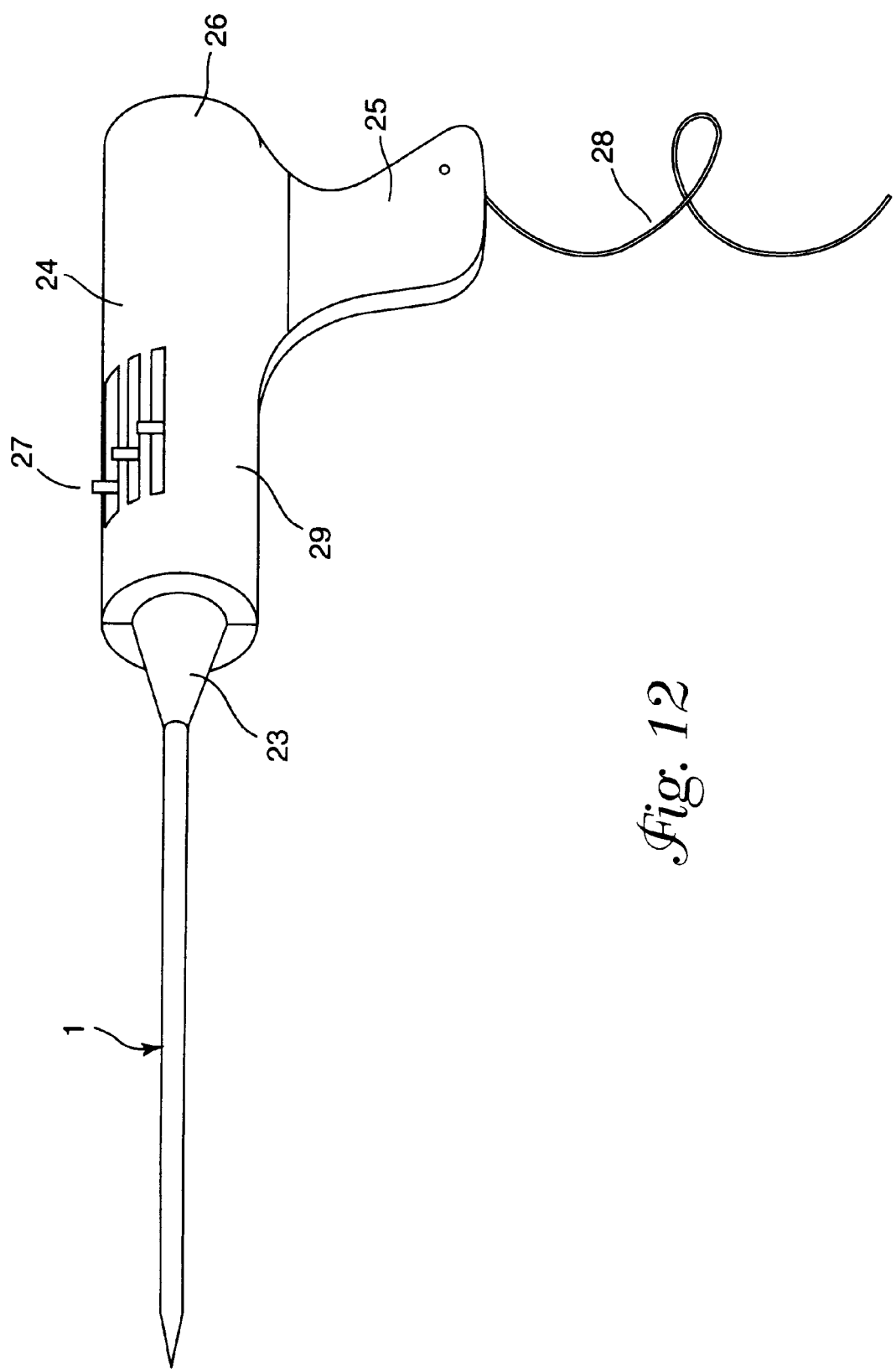

TUMORTHERAPY DEVICE AND METHOD

The present invention claims priority to German patent application 198 06 693.7, filed Feb. 16, 1998, the entire disclosure of which is incorporated herein by reference.

FIELD OF THE INVENTION

The present invention is directed to minimally invasive surgical procedures. Specifically, the invention is directed to minimally invasive devices and methods for removal of a consolidated tissue mass from a dense tissue.

BACKGROUND OF THE INVENTION

Generally, solidated tissue masses, such as a tumor, which are situated deeply in a dense tissue have to be removed by an open surgical cut down through the dense tissue and around the consolidated mass. Such tumors include, for example, tumors of the breast, prostate, liver, muscle and fatty tissue. Presently, there are no minimally invasive systems to access the tumor for removal. The advantage of minimally invasive procedures performed in body cavities, for example, laparoscopy and arthroscopy, are well known.

Using a minimally invasive "key hole" method for tumor removal for accessing the tumor through a small incision in a dense tissue could reduce tissue trauma and pain and enhance patient recovery time.

SUMMARY OF THE INVENTION

The present invention provides minimally invasive systems for removal of consolidated tissue masses, such as tumors or other pathological tissues, located deep to the surface of a dense tissue. In general, the present invention is directed to a system of telescoping needles and cannulas. In some embodiments, the operation of a system of the invention can be facilitated by guidance of MRI visualization.

Throughout the present disclosure, examples are provided for illustration purposes. The examples are not intended to limit the invention. Thus, for example, when a device or method is described with regard to breast tissue or a tumor, it will be appreciated that the procedure is equally applicable to other tissues as further described below.

As used herein, a "needle" refers to an elongate hollow or solid centered body having a proximal end and a distal end. The distal end is the end directed toward the patient and the proximal end is the end facing the operator during use. A needle of the invention includes a sharp distal end which can pierce, cut or penetrate a tissue.

As used herein, a "cannula" refers to an elongate hollow body having a proximal end and a distal end. The proximal and distal end are as defined above. In some embodiments, a cannula of the invention can include a mechanism for excising or cutting a consolidated tissue mass at the distal end.

The invention provides for deep dissection of a dense tissue by step by step (incremental) mechanical widening or separation of the tissue. Generally, a device disclosed herein includes a telescoping needle system comprising an inner guiding needle, a system of one or more tissue separating needles to widen, stretch or otherwise separate the tissue, and an outer needle which defines an operating lumen. As used herein, the "operating lumen" is the lumen of the outermost needle used to perform a procedure of the invention. In some embodiments, the inner guiding needle can be a biopsy device. In one simple embodiment, only a single needle with a cone-shaped tip is inserted into the tissue so that it is widened and stretched. However, generally the invention provides a plurality of telescoping needles which are inserted sequentially into the dense tissue to widen the tissue step by step.

In a preferred embodiment, the outer needle includes an operating lumen having a longitudinal slit. The longitudinal slit includes a first and second lateral edge that move apart from one another when widening needles are inserted within the operating lumen of the outer needle, thus increasing the diameter of the operating lumen. In one embodiment, after placement, the operating lumen of the outer needle can be reduced in size to peripherally compress a consolidated tissue mass when the separating needles within the operating lumen of the outer needle are removed in a proximal direction. Thus, when the outer hollow needle has been placed around a tumor, for example, it can press the tumor and hold it fast in its lumen.

Such a held fast tumor can be removed with various cutting instruments. In one embodiment, a tumor can be pressed and cut out. Typically, if the tumor was in slack tissue, a cutting instrument may not be able to grasp it.

BRIEF DESCRIPTION OF THE DRAWINGS

FIGS. 1a–c illustrate a first embodiment of a telescoping device according to the invention.

FIGS. 2a–h are longitudinal cross section views illustrating removal of a consolidated mass from a dense tissue using the device of FIGS. 1a–c.

FIGS. 3a–h are longitudinal cross section views of a second embodiment of a device according to the invention illustrating removal of a consolidated mass from a dense tissue.

FIGS. 5a–c are transverse cross section views taken at 5a—5a, 5b—5b and 5c—5c of FIGS. 3c, 3f and 3g, respectively.

FIGS. 7a–b are longitudinal cross section views of different embodiments of the distal tip of a tissue separating needle.

FIG. 12 is a perspective view of one embodiment of a device for automatic advancement of the needles of a telescoping system of the invention.

DETAILED DESCRIPTION OF THE PREFERRED EMBODIMENT

Figure 2G:
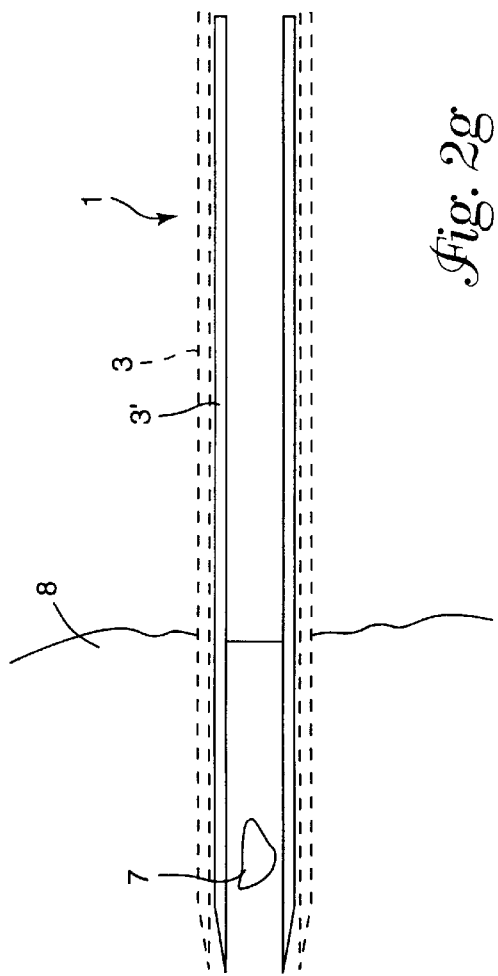

According to the illustrated embodiments, the invention is directed to advancing a small-gauge needle close to a consolidated tissue mass and to pass one or more additional needles to separate or widen the tissues surrounding the mass to form a minimally invasive opening through which the mass can be removed from the surrounding tissue. Once the surrounding tissue is sufficiently widened, an outer (hollow) needle with a longitudinal slit can be inserted and guided to the tumor over the widening needles. The outer needle can then be positioned to peripherally surround the tumor. If all inner needles are removed, the lumen of the outer needle preferably contracts (i.e., the stress of the expanded lumenal wall of the outer needle is reduced) and holds the tumor fast (snugly) at its distal end. Once held firmly, the mass can be removed precisely with a cutting instrument.

As used herein, a "consolidated tissue mass," "consolidated mass" or "mass" refers to a normal or abnormal (e.g., pathological) tissue mass having a substantially defined margin. Preferably, the margin is readily distinguishable from the surrounding tissues. Examples include tumors (benign or malignant), abscesses, lipomes, etc.

The devices and methods of the invention are particularly advantageous for accessing or removing a tissue mass located in a dense tissue. As used herein, a dense tissue refers to tissues including, for example, muscle, skin, brain, fat, lymph node, mammary gland, and including parenchymal organs such as liver, spleen, kidney, prostate, etc. It will be appreciated that the invention is suitable for use with a human or animal patient.

The invention provides for incrementally widening or stretching a small hole in a dense tissue initially created by a small gauge inner needle. Subsequently, additional needles are passed over the proximal end of the previous needle. Each needle further separates the dense tissue surrounding a tissue mass to provide an opening of sufficient diameter for exteriorizing the tissue mass. The invention will now be more fully described by reference to the illustrations.

FIG. 1 shows the principle of the telescoping device 1 in a simple example. In this embodiment, the device comprises inner guiding needle 2, outer (hollow) needle 3 having longitudinal slit 5 and inner widening (tissue separating) needle 4. The needles include a sharp penetrating end 6a, such as a bevel 6 at the distal end of the needle.

FIGS. 2a–h show a working principle of the device of FIG. 1. As illustrated, device 1 is placed onto the surface of a dense tissue such as the breast. Inner guiding needle 2 is inserted into the breast tissue 8 and advanced forward to tumor 7, FIG. 2b. Then, a first inner widening needle 4 is inserted over guiding needle 2 into the tissue 8, FIG. 2c. As a result, the breast tissue is widened (separated) to the diameter of widening needle 4, FIG. 2d. Subsequently, outer needle 3 is pushed over widening needle 4, FIG. 2e, and placed around tumor 7, FIG. 2f. Tumor 7 is now situated inside the distal end of the operating lumen of outer hollow needle 3.

Referring to FIG. 1b, outer hollow needle 3 is preferably manufactured with a longitudinal slit 5, which is closed or in a "neutral position" when edges 30 and 31 meet. If hollow needle 3 is widened as described above by insertion of one or more widening needles, slit 5 opens and edges 30 and 31 of the slit move away from one another. In this position, the wall of outer needle 3 is mechanically stretched.

Figure 2H:
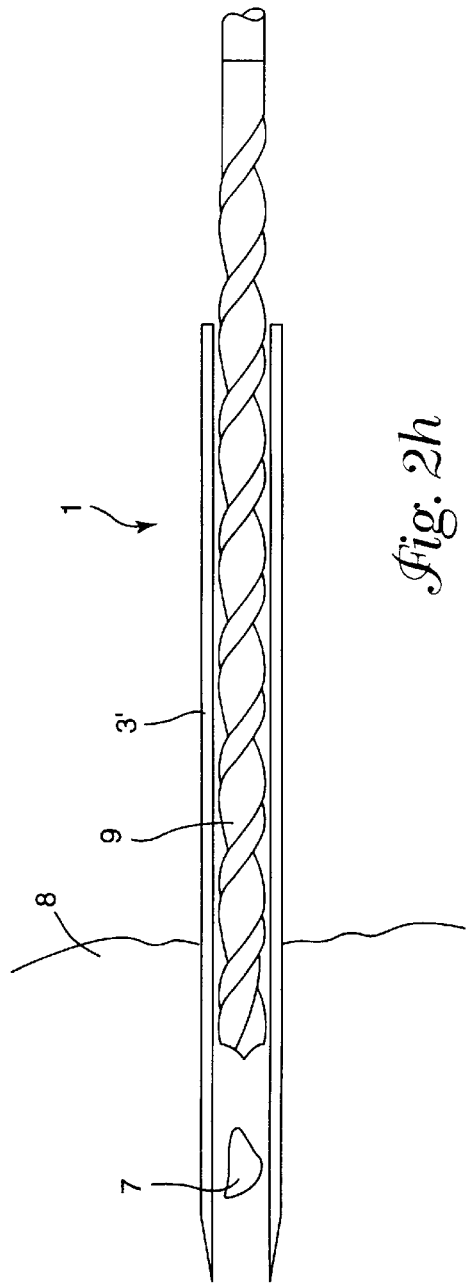

Thus, after inner guiding needle 2 is inserted into the tissue, additional widening needles are sequentially telescoped over one another until the lumen of outer needle 3 can be mechanically stretched to a size sufficient to surround the lateral margins of the mass. After advancing outer hollow needle 3 in spread (expanded) position over the tumor, FIG. 2f, inner guiding needle 2 and widening needle 4 are removed in a proximal direction. Referring to FIG. 2g, removal of widening needle 4 relieves mechanical stress of the hollow needle 3 and hence, diameter 3 reduces to diameter 3'. Thus, tumor 7, which is situated in the distal lumen of outer hollow needle 3, is squeezed by the wall of the needle 3' and the tumor held fast inside the operating lumen. The stabilized tumor can be cut and removed from the dense tissue easier and more cleanly than if free floating in slack tissue. FIG. 2h shows one instrument 9 for destroying the tumor that is pinched into needle 3'. Instrument 9 functions by screwing in a cutter similar to a die-tap.

In a preferred embodiment, the system comprises a large number of widening needles 4, which provide for incrementally widening and stretching the access site with minimal trauma cause, for example, by cutting the dense tissue.

The wall thickness of a widening needle ranges from about 0.05 mm to about 5 mm. A Typical wall thickness ranges from about 0.5 mm and 2.0 mm. In one embodiment, the device includes 1 to 20 widening needles of the same or various wall thicknesses. The widening needles can be advanced into the tissue towards the tumor at the same or different rates of speed.

Furthermore, the widening needles can be moved forward simultaneously or one after the other, without a time overlap, and with the same or different velocity.

Figure 3A:
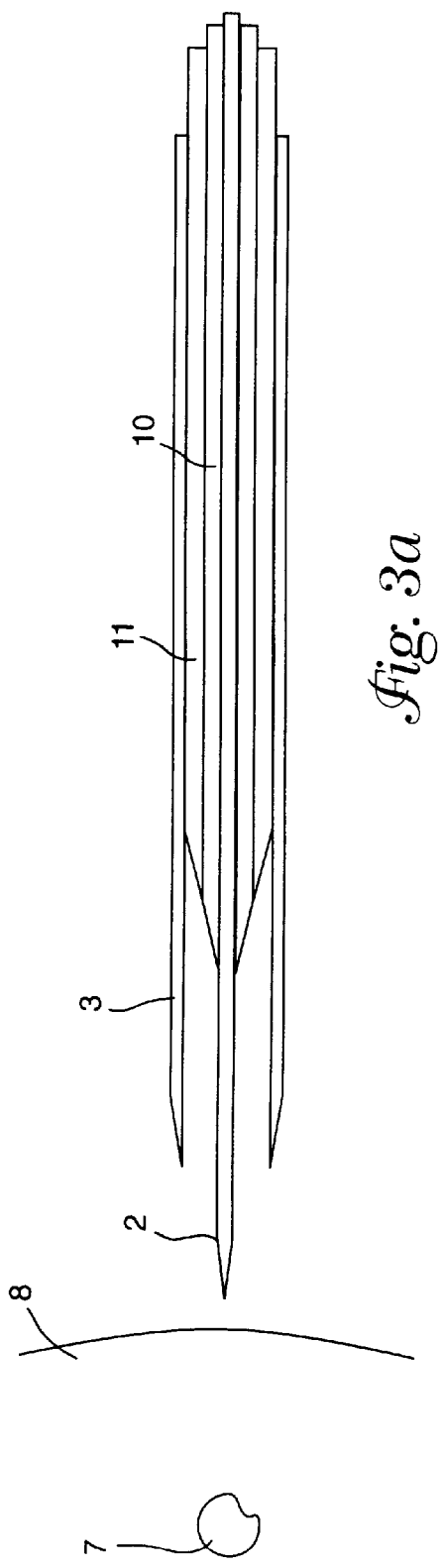
Figure 3B:
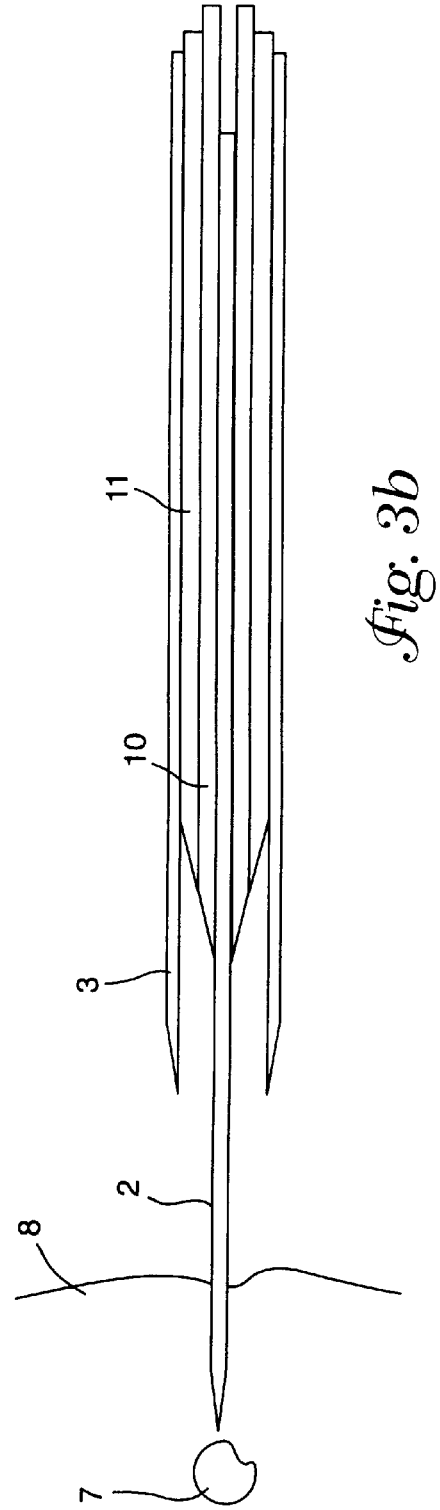

Referring now to FIGS. 3a–h, only two widening needles 10 and 11 are inserted with one over the other and one after the other at the same velocity towards the tumor 7. Outer hollow needle 3 has a longitudinal slit (see FIGS. 5b–c) and provides for grasping the tumor. As illustrated in FIG. 3a, the system is placed onto the breast tissue 8, and inner guiding needle 2 is inserted into the tissue and guided to tumor 7, FIG. 3b. An inner widening needle 10 is pushed over the guiding needle 2 and a further widening needle 11 over the inner widening needle 10, FIG. 3c and FIG. 3d. Outer hollow needle 3, with longitudinal slit 5, is pushed over the system of widening needles 10 and 11, FIG. 3e, and over the tumor. In FIG. 3g, widening needles 10 and 11 have been removed in a proximal direction causing the stress of outer hollow needle 3 to be relieved, thus reducing the inner diameter of the lumen and pinching the tumor within the inside of the outer needle. In FIG. 3h, a cutting instrument 9 is used to extract the tumorous tissue.

FIGS. 5a–c are transverse cross section views of the device of FIG. 3 at various points during the procedure. FIG. 5a is taken at line 5a—5a of FIG. 3c wherein inner widening needle 10 is pushed into the tissue. FIG. 3d shows how outer widening needle 11 is pushed over inner widening needle 10. FIG. 5b is taken at line 5b—5b of FIG. 3f and shows how outer hollow needle 3 encircles inner guide needles 2 and widening needles 10 and 11. It will be appreciated that slit 5 of outer hollow needle 3 is opened widely. FIG. 5c is taken at line 5c—5c of FIG. 3g. After having removed widening needles 10 and 11, in proximal direction, outer hollow needle 3 relieves its stress and the slit 5 closes. Thus, the tumor is compressed as outer needle 3 contracts from diameter X' to diameter X. Compare FIGS. 5b and 5c.

Referring to FIG. 3f, one advantage of the disclosed invention is that only tissue inside the distal part 32 of outer hollow needle 3 is extracted. By separating the surrounding dense tissue 8 according to the invention, when the device 1 is removed, the tissue in the region 33 between the surface of the dense tissue 8 and the tumor 7 is only compressed and/or stretched. Thus, the method of the invention is less traumatic than prior methods.

Figure 4A:
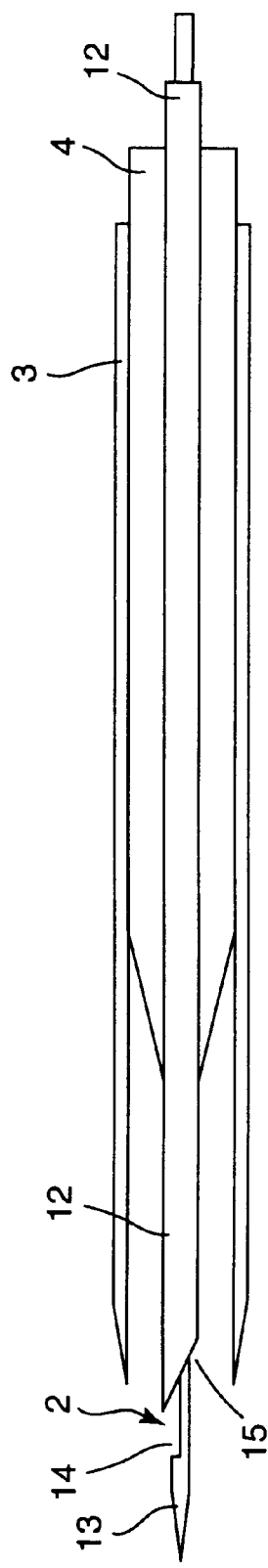
FIGS. 4a–b are a longitudinal cross section and profile view, respectively, of an inner needle configured and arranged for taking a biopsy sample.
Figure 4B:
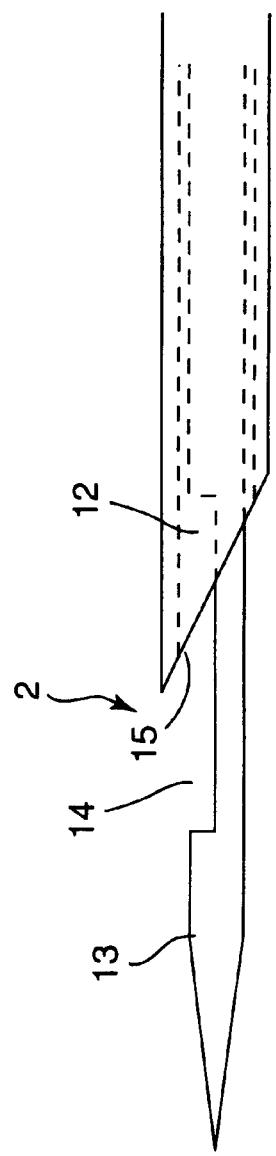

Before removal of a tumor, it may be advantageous to determine the histopathology of the tumor. Generally, a tissue sample can be obtained by a biopsy. FIG. 4 shows one embodiment of the invention integrating a biopsy device into the inner guiding needle 2. According to this embodiment guiding needle 2 comprises an outer biopsy needle 12 which can cut a biopsy sample with its sharpened tip 15. According to this illustrated embodiment, the biopsy sample is collected in notch 14 of inner biopsy needle (obturator) 13. FIG. 4b is a close up view of the distal part of the biopsy system of FIG. 4a. The illustrated biopsy system functions similar to known SideCut, TruCut or SideSlit biopsy needles. The obturator 13 is arranged with outer biopsy needle 12 so that notch 14 can be exposed or unexposed. In use, tip 15 of biopsy needle 12 is advanced distally close to the tumor. Obturator 13 is then pushed forward into the tumor until the tumor fills in notch 14. Outer biopsy cannula 12 is then moved forward cutting the tumor with sharpened edge 15 and collecting a part of the tumor in notch 14. Obturator 13 can then be removed from outer biopsy needle 12 in a proximal direction and the tissue sample can be removed for examination by a diagnostic laboratory. The obturator 13 can be reused or a replacement obturator 13 can be passed into the outer biopsy needle 12 for collecting additional samples. The bevelings of the needles can be made as proposed in DE 295 13 981.1. The entire disclosure of DE 295 13 981.1 is incorporated herein by reference.

In addition, other types of biopsy instruments can be used. For example, guiding needle 2 can comprise an aspiration biopsy device, a biopsy punch, a biopsy device with a rotating cutting edge, etc.

Advantageously, the present device 1 can provide for diagnosis and therapeutic removal of a tumor in a single procedure. Thus, a radiologist or other clinician who obtains the biopsy sample can await the laboratory report and perform the therapeutic removal operation immediately using the same device.

In one embodiment, the invention provides a kit including a therapeutic tumor removal system and instrumentation for obtaining a biopsy sample. Thus, after taking a biopsy sample, if the laboratory report indicates, complete removal of the tumor can be performed.

The devices and methods of the invention are especially useful under diagnostic imaging systems such as MRI, CT, ultrasound or X-ray. In order to use the system under MRI, the system needles are preferably manufactured from a low magnetic material such as titanium alloy as described in DE 195 311 17.5-35, the entire disclosure of which is incorporated herein by reference. Other suitable materials include stainless steel or nickel alloys. Spring steel or super elastic or pseudoelastic nickel-titanium are particularly suitable for an outer hollow needle.

Figure 6:
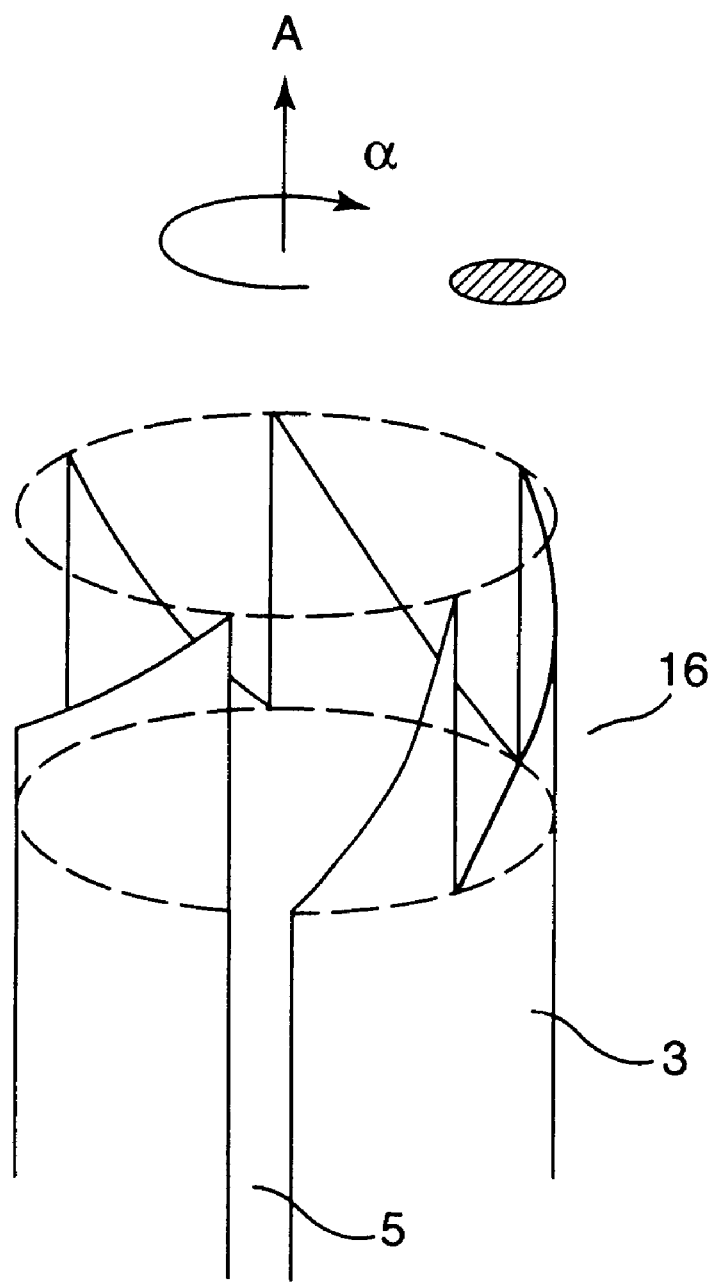
FIG. 6 is a perspective view of a distal tip of an outer needle.

Often times, tissue resistance may make it useful to advance the needles while rotating rather than pushing directly into the tissue. This may be particularly true for the outer hollow needle 3. FIG. 6 shows an embodiment of a hollow needle 3 having a beveled distal tip. The illustrated "cutting beveled edge" is made so that there are some faced or unfaced cutting teeth 16, which cut the tissue when rotated in the direction of a and simultaneously advanced in direction A. Thus, teeth 16 can cut when the needle is rotated to the right or left. FIG. 6 also shows the longitudinal slit 5 of outer hollow needle 3.

It will be appreciated that during a dissecting procedure, blood can pass aproximally through the needles. In addition, blood can be aspirated in proximal direction by means of an aspiration system e.g., with a drip pan or a connector for an aspiration set.

FIGS. 7a–b illustrate that the distal tip of widening needles 4, 11 or 12 can be a beveled cone shape 17, a convex shape 18, concave shape or other profile shape.

Figure 8A:
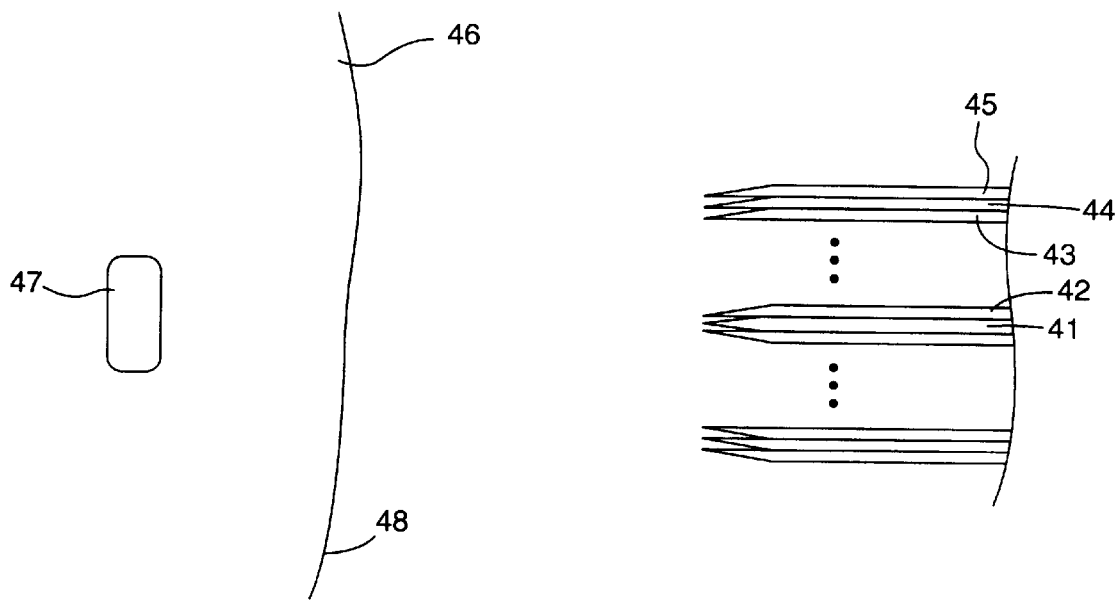
FIGS. 8a–d are longitudinal across section views of another embodiment of a device of the invention illustrating removal of a consolidated mass using a large number of separating needles.
Figure 8B:
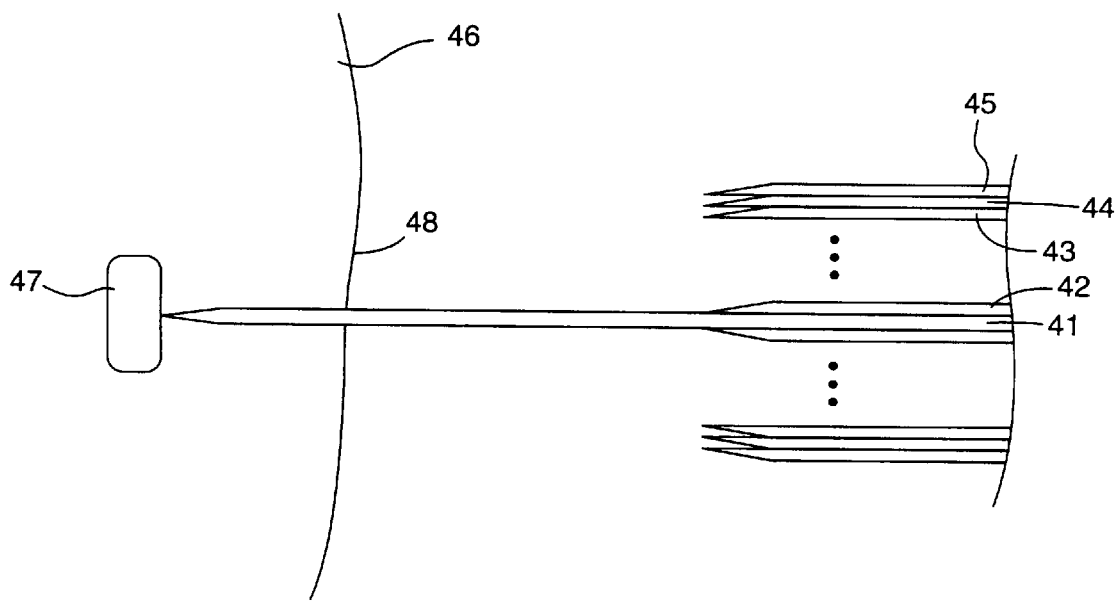
Figure 8C:
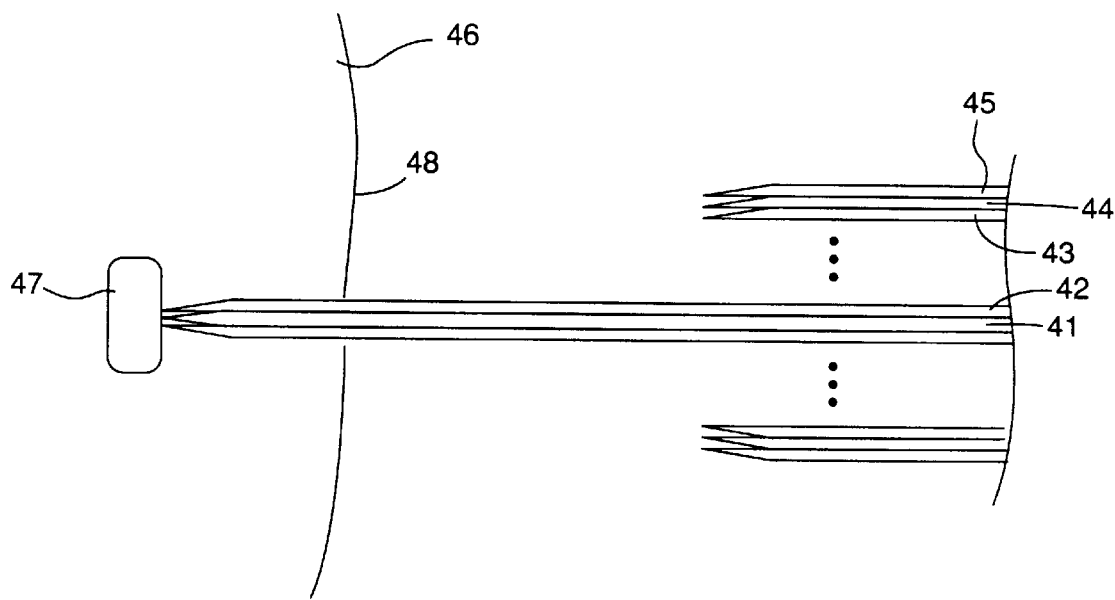
Figure 8D:
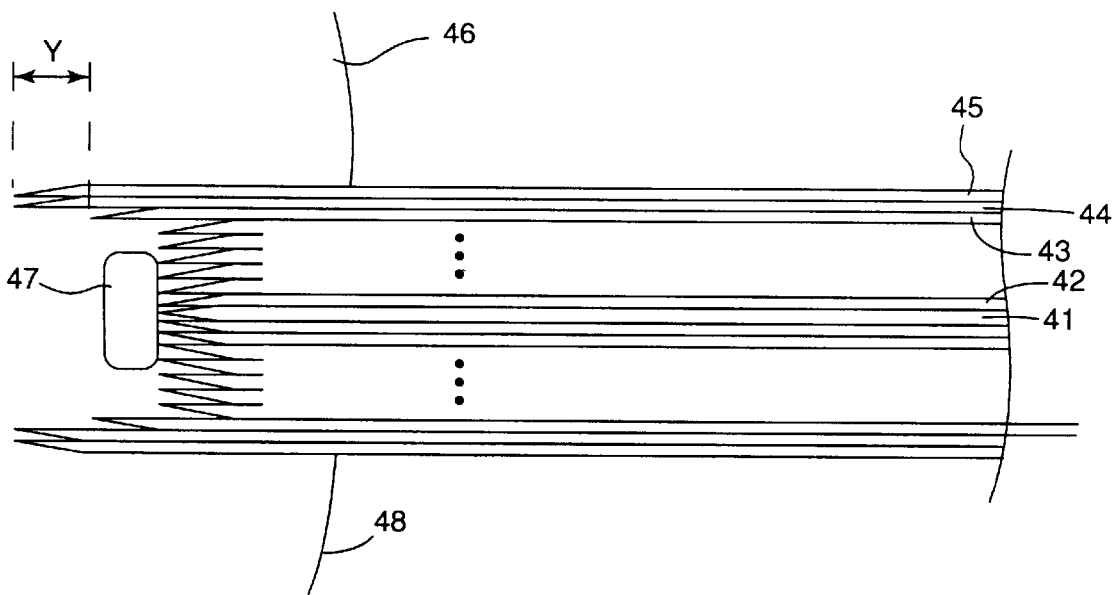

FIGS. 8a–8d illustrate a system of telescoping needles which can widen dense tissue 46 according to the invention. As stated earlier, an inner needle 41 can be a biopsy device, as shown in FIG. 4. In the present embodiment, a first widening needle 42 and further widening needles, illustrated as three dots, are around inner needle 41. The outer system comprises an outer needle 45, a second outer needle 44 and third outer needle 43. In this embodiment, outer needle 45 does not include a slit. Referring to FIG. 8b, to remove a tissue mass, inner needle 41 is inserted and pushed forward to the tumor. Then, outer needles 42–45 are inserted, FIGS. 8c–8d. As seen in FIG. 8d a large number of outer needles can be used to encircle a tumor 47 in tissue 46 by, for example, a third outer needle 43, a second outer needle 44 and outer needle 45. In FIG. 8d, the skin 48 is stretched and very taut. However, generally, the deeper the needles must be inserted to reach the tumor 47, the less the tissue is stretched.

FIG. 9 shows a tumortherapy procedure using a cutting thread which can be selectively tensed to create a cutting instrument. According to this procedure, after widening the tissue as shown in FIG. 8d, outer needle 45 is advanced beyond the depth of tumor 47 and second outer needle 43. Distance Y results from the difference between the distal tip of outer needle 45 (and second outer needle 44) and the distal tip of third outer needle 43. Referring to FIG. 9a, all inner needles are now removed except third outer needle 43. This then creates a channel between outer needle 45 and third outer needle 43. A cannula 49, shown in FIG. 9c and 9d is then pushed into the channel created.

Figure 9A:
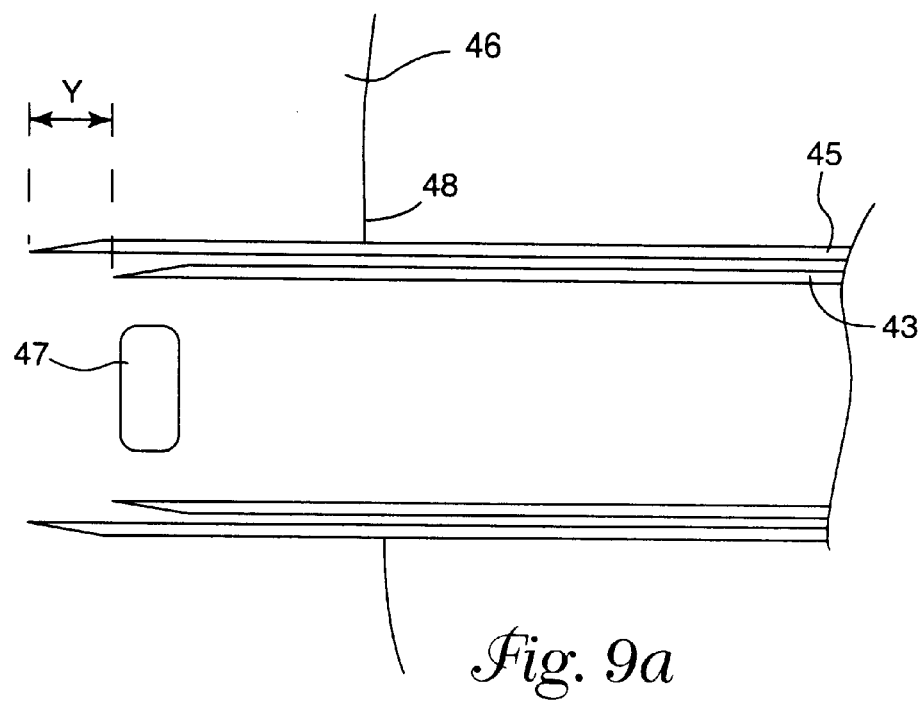
FIGS. 9a–g illustrate an embodiment of a tumor therapy procedure and device for excising a consolidated mass.
Figure 9B:
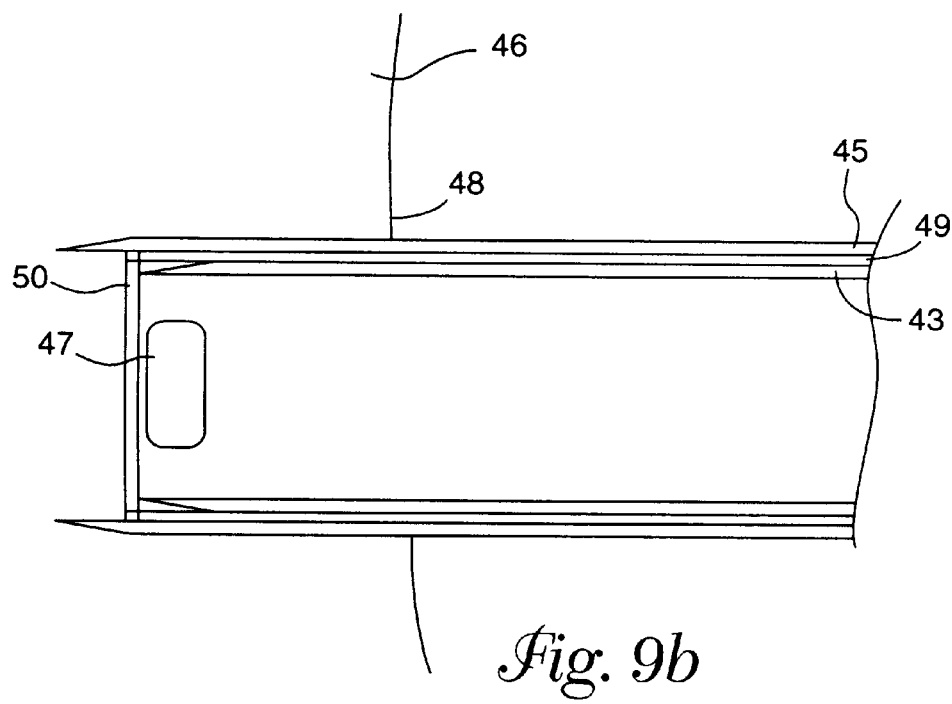
Figure 9E:
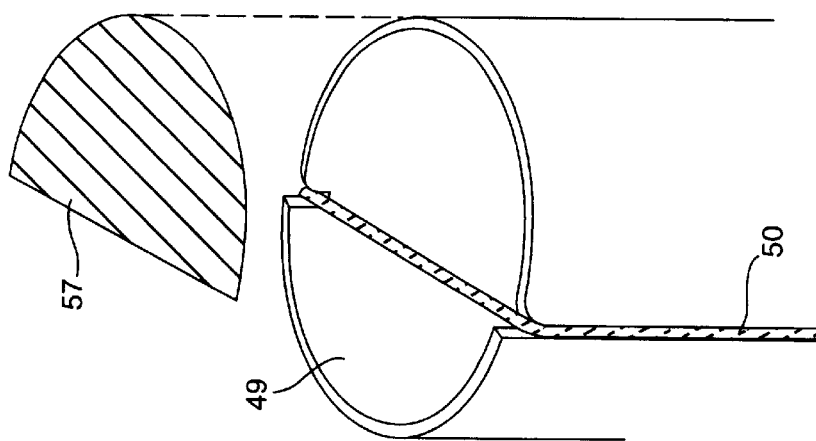
Figure 9D:
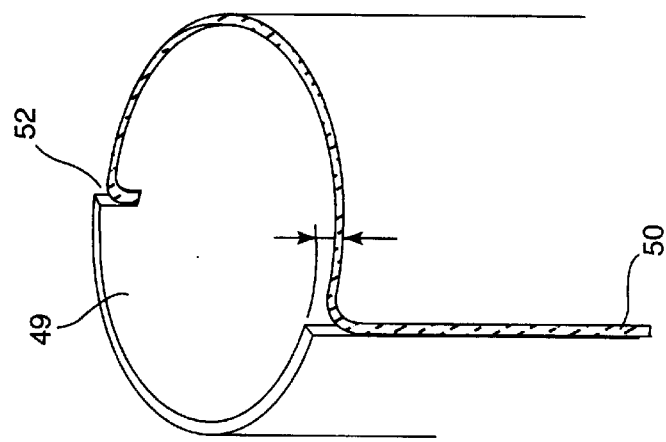
Figure 9C:
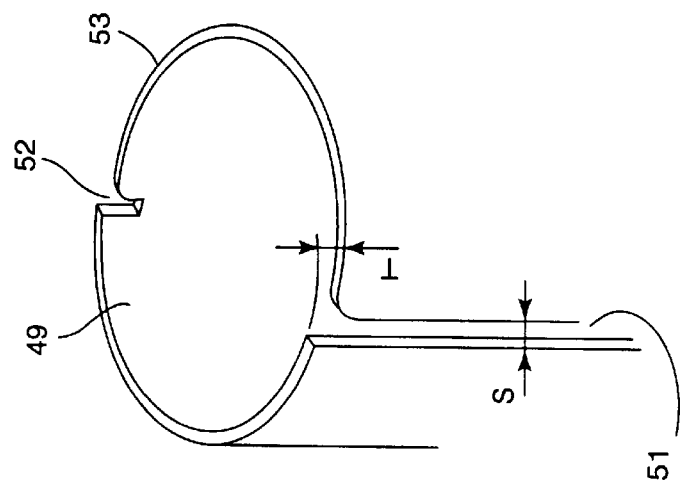

Referring to FIGS. 9c and 9d cannula 49 is provided with a longitudinal slit 51 having a breadth (gap) S. Opposite this longitudinal slit 51, (i.e., about 180° around the longitudinal axis of cannula 49), is groove 52. In this embodiment, a semicircumferential recess 53 courses around about one half the circumference of the distal opening of cannula 49. The recess extends proximally into the cannula wall to a depth of T. A thread 50 can be located in such a structure. As illustrated, thread 50 can be connected tightly in groove 52 of cannula 49 using suitable methods. The thread 50 can lie loosely on the distal end of cannula 49 on the distal edge of recess 53. The thread can lie in this location because the thickness of thread 50 and wall thickness of cannula 49 are about the same and because it is held on the sides between outer cannula 45 and third outer cannula 43.

Cannula 49, with thread 50, can be pushed from a proximal to distal direction through the channel between outer needle 45 and third outer needle 43 until the recessed distal edge of the distal end of cannula 49 is extended slightly beyond the distal end of outer needle 43. If cutting thread 50 is pulled in the direction of the arrow (proximal) as shown in FIG. 9e, it cuts through the tissue at the distal end of cannula 49 in semicircular 57 manner. If cannula 49 with tensed thread 50 is rotated 180° around its longitudinal axis, thread 50 then also cuts distal to the second half of the tumor in the lumen of cannula 49. The thread 50 is tensed over third outer needle 43. After this procedure, cannula 49 can be rotated another 90° around the longitudinal axis and thread 50 may be released so that cannula 49 and third outer needle 43 can be taken out in a proximal direction and, at the same time, tumor 47 is removed in proximal direction.

Figure 9G:
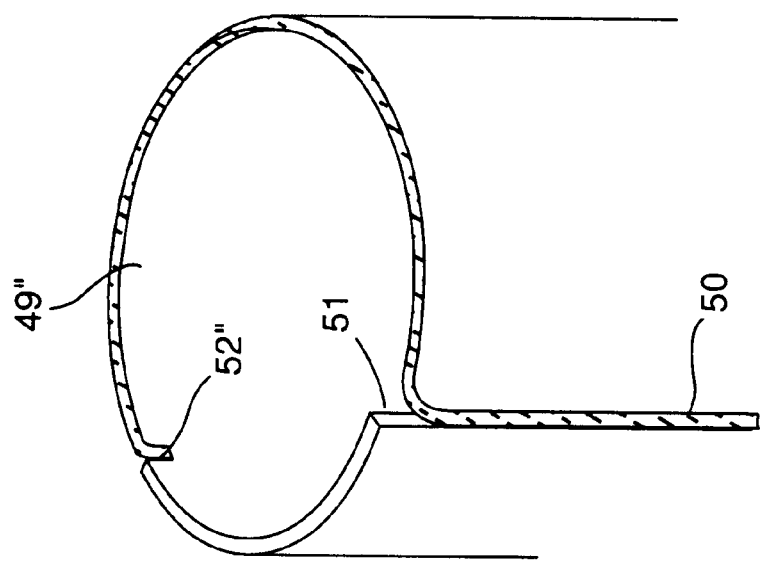
Figure 9F:
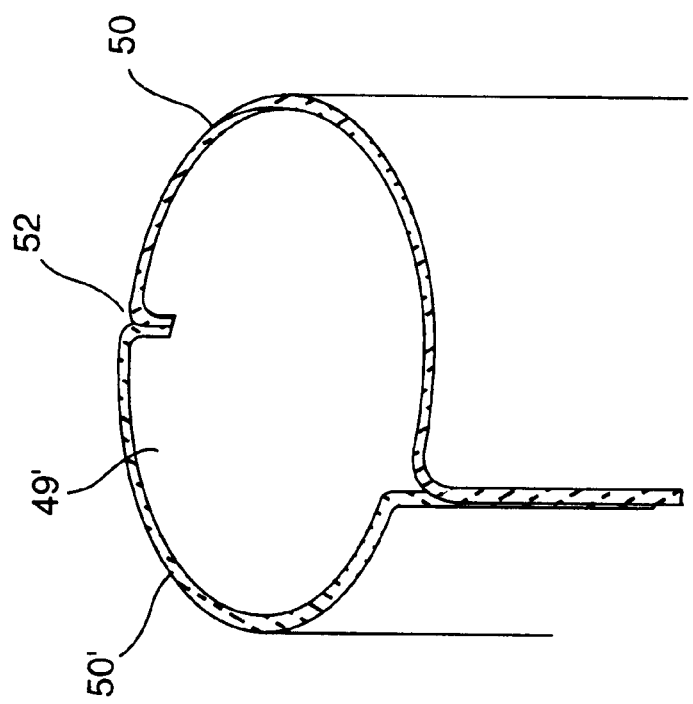

As illustrated in FIG. 9f, a cannula 49' can have two or more cutting threads 50 and 50'. In other embodiments, as illustrated in FIG. 9g, groove 52" is not situated diametrically opposite groove 51. In addition, in some embodiments, recess 53 is not present. As illustrated in FIG. 9f, thread 50 and 50' can lie loosely on the end of the cannula.

Figure 10A:
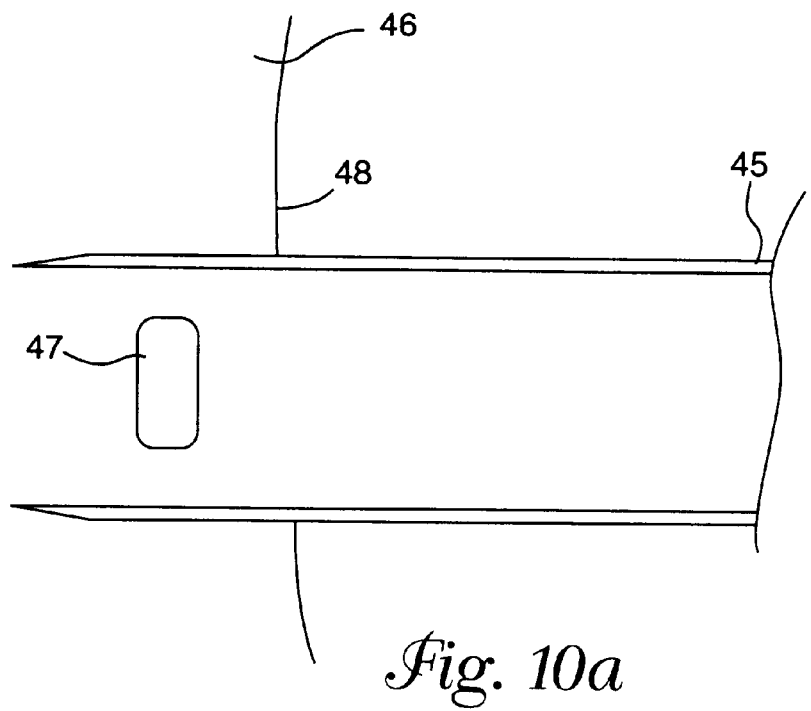
FIGS. 10a–d illustrate another embodiment of a tumor therapy procedure and device for excising a consolidated mass.
Figure 10B:
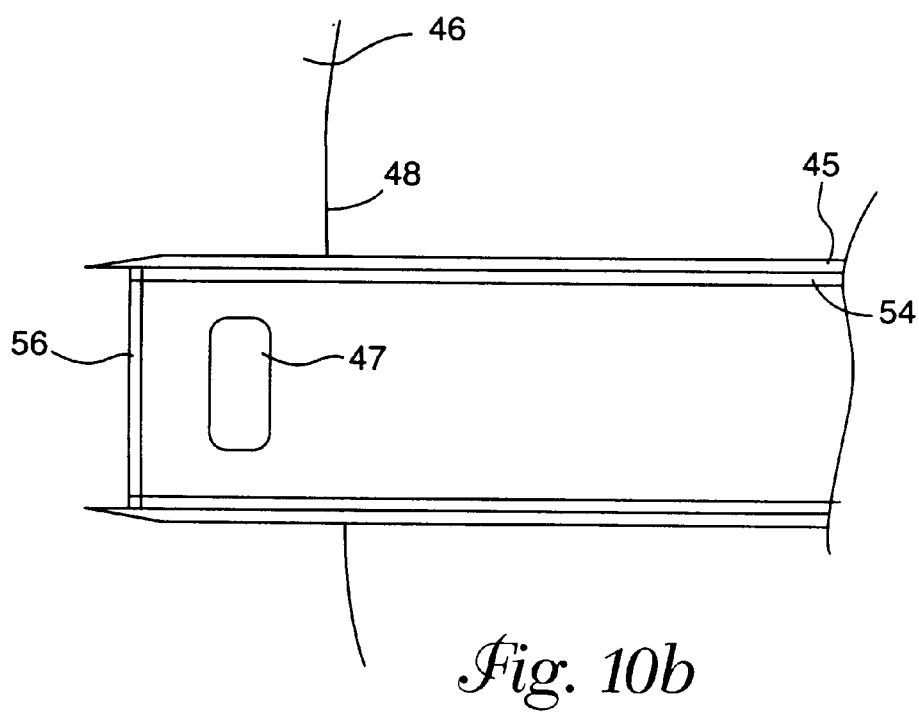
Figure 10D:
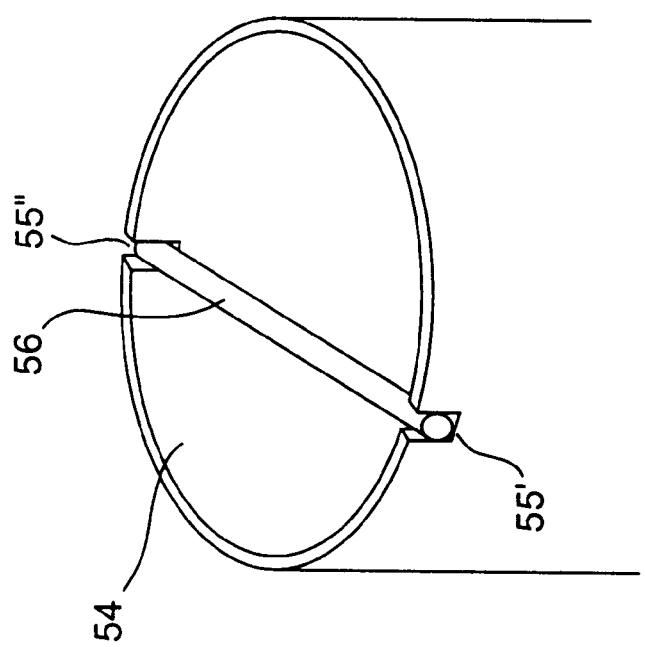
Figure 10C:
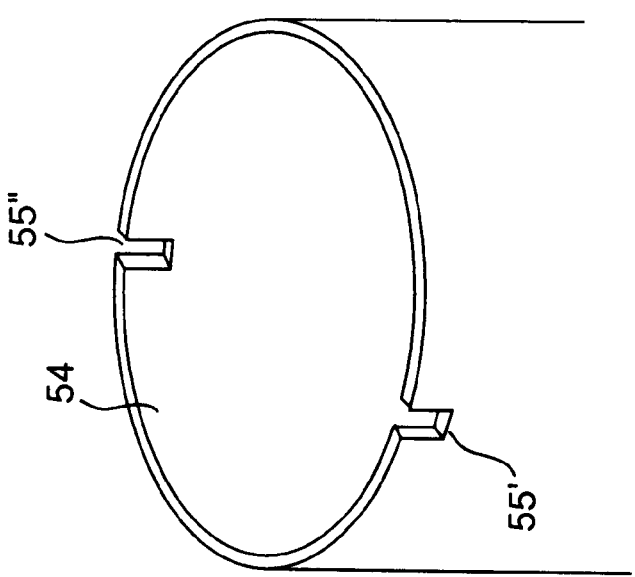

FIGS. 10a–d show how tumor 47 can be removed with a pretensed thread 56. Starting with the needle configurations as shown in FIG. 8d, all inner needles 41–44 are removed in a proximal direction, so that only outer needle 45 remains in tissue 46. Now, cannula 54 is pushed from a proximal to distal direction through needle 45. Cannula 54 is shown in FIGS. 10c and d. As illustrated, cannula 54 has two grooves 55' and 55" which are situated diametrically opposite to each other at the distal end of cannula 54. A cutting thread 56 is fixed in grooves 55' and 55" so that it is tensed between the two grooves. Thread 56 can be, for example, welded in place. The thread 56 can be a wire of stainless steel, titanium, or other suitable material for cutting. As cannula 54 is pushed from a proximal to distal direction past tumor 47, cutting thread 56 cuts through the tumor by the time the distal end of cannula 54 is in the position illustrated in FIG. 10b. If cannula 54 is positioned as shown in FIG. 10b, rotating the cannula 54 360° around its longitudinal axis cuts out the part of the tissue defined by the lumen of cannula 54. If it is turned by another 90° and removed in proximal direction it extracts the cut out tissue over cutting thread 56 in proximal direction.

In addition, an instrument for removing a tumor that is excised by a cannula device as shown in FIGS. 9 and 10 can be constructed for removing the tumor from a distal to proximal direction. Such an instrument can include a corkscrew type distal end which is screwed into the excised tissue by a sufficient distance to be able to remove the tumor in a proximal direction.

Figure 11:
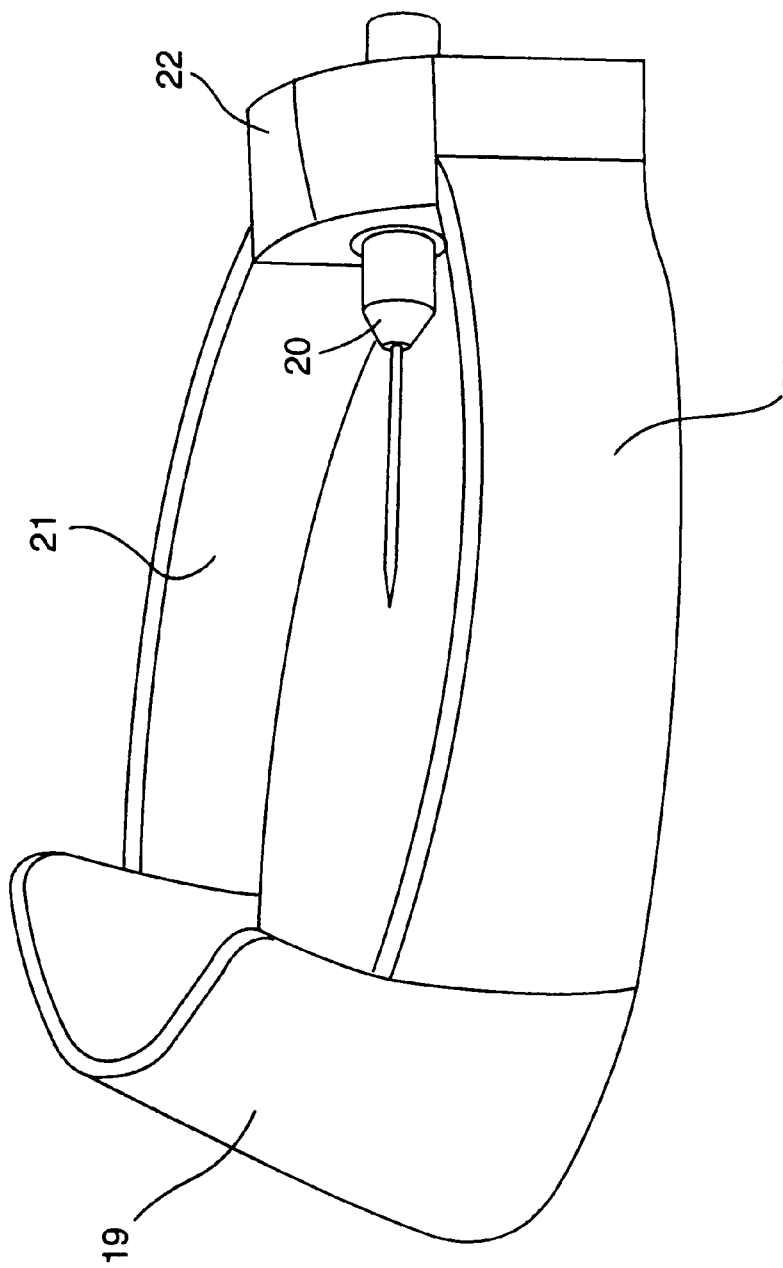
FIG. 11 is a perspective view of a holding device for stabilizing a dense tissue for tumor therapy according to the invention.

In some circumstances, it may be advantageous to apply a counterpressure to stabilize a dense tissue for tumortherapy according to the invention. FIG. 11 shows one embodiment of a construction for stabilizing a dense tissue such as a breast. According this embodiment, the breast is held in holding device 19 in a selected fixed position. Two connecting parts 21 of holding device 19 are connected by seat 22 of gear. Needle gear 20 controls the advancement of the single needles: the inner guiding needle, the widening needle and the outer hollow needle with slit. The needle gear also defines the advance speed, the insertion depth, the rotation speed and the proximal distances between all needles. The needle gear can be driven by hand or by motor. If the needle gear is motor operated and the dissecting procedure is to be performed in an MRI field, the motor should be selected to avoid creating an artifact on the MRI image. DE 197 092 67.5 discloses a suitable ultrasound motor for this purpose and the entire document is incorporated herein by reference. Alternatively, a pneumatic or hydraulic drive or a flexible or rigid shaft motor which is connected to an electromagnetic motor situated outside the MRI machine.

FIG. 12 shows an example of a hand held driving motor system 24. In the illustrated embodiment, needle system 1 is connected by means of needle changer 23 to the handheld system 24 for automatic needle advancement. System 24 comprises a driving part 29 and gear 26, which may function as described above. The system 24 includes a handle 25 for holding and the needles are operated by switch and lever 27. If handheld system 24 is electrically driven, it can include a power cord 28 or it can be battery operated. System 24 can also be driven by hand.

After the dense tissue has been dissected to access a tumor according to the invention, the tumor can be removed by cutting, laser, high frequency coagulation, water irrigation including a water jet, or other similar method.

The needles of the present invention can be reusable or disposable. In addition, a system for needle advancement can also be reusable or disposable.

From the foregoing detailed description, it will be evident that modifications and variations can be made in the devices and methods of the invention without departing from the spirit or scope of the invention. Therefore, it is intended that all modifications and verifications not departing from the spirit of the invention come within the scope of the claims and their equivalents.

We claim:

1. A device for removal of a consolidated mass located within a dense tissue comprising:
   a telescoping system of needles including:
   (i) an inner guiding needle;
   (ii) at least one tissue separating needle having a distal cutting edge and surrounding the inner guiding needle; and
   (iii) an outer needle defining an operating lumen to receive the at least one tissue separating needle.

2. A device according to claim 1, wherein the outer needle includes a longitudinal slit for expansion and contraction of the operating lumen such that when the device is positioned in the dense tissue, expansion of the operating lumen of the outer needle by the at least one tissue separating needle separates the dense tissue and removal of the at least one tissue separating needle contracts the operating lumen.

3. A device according to claim 1 comprising at least two tissue separating needles wherein removal of one of the two separating needles adjacent to the outer needle provides a gap into which a cannula can be inserted.

4. A device according to claim 3 wherein the cannula has a proximal end and a distal end, the distal end including a mechanism for excising the consolidated mass, the mechanism comprising:
   (a) a cutting thread;
   (b) an arrangement for fixing the cutting thread to the distal of the cannula; and
   (c) a semicircumferential recess at the distal end of the cannula.

5. A device according to claim 3 wherein the cannula has a proximal end, a distal end and a lumen, the distal end having a cutting wire fixed across a diameter of the distal end of the lumen of the cannula.

6. A device according to claim 1 wherein the device is manufactured from materials selected from the group comprising titanium alloys, nickel alloys, nickel-titanium and stainless steel.

7. A device according to claim 1 wherein the inner guiding needle is a biopsy needle comprising an outer biopsy needle and an obturator needle having a notch and wherein the obturator needle can be removed in proximal direction to collect a bioptic tissue sample.

8. A device according to claim 1 wherein the inner guiding needle comprises an aspiration needle.

9. A device according to claim 1 wherein inner guiding needle comprises a biopsy device with a rotating cutting edge.

10. A device according to claim 1 wherein a distal end of the at least one tissue separating needle or a distal end of the outer needle include one ore more cutting teeth.

11. A device according to claim 1 wherein a distal end of at least one of the at least one tissue separating needle includes a beveled needle edge that is cone shaped or convex.

12. A device according to claim 1 further comprising a drive motor for distally advancing the at least one tissue separating needle.

13. A device according to claim 1 wherein the drive motor is selected from a group of motors comprising: pneumatic, hydraulic, linear, rotational and piezoelectrical ultrasound motor.

14. A device according to claim 1 wherein the at least one tissue separating needle is hand driven.

15. A device according to claim 1 wherein the device is formed from materials that produce low levels of magnetic artifact in a magnetic resonance imaging field.

16. A device according to claim 1 wherein the device further comprises a holding apparatus and wherein the holding apparatus comprises:
   a securing arrangement for securing the dense tissue in the holding device in a selected position; and
   a mechanism for advancing at least one of the needles of the telescoping system of needles.

17. A method for removing a consolidated mass from a dense tissue comprising a step of:
   accessing the consolidated mass in the dense tissue by inserting a system of telescoping needles having distal cutting edges to puncture skin and incrementally separate the dense tissue to create an opening through which the consolidated mass is accessed; and
   removing the consolidated mass through the opening.

18. A method according to claim 17 wherein the dense tissue is incrementally separated using a device comprising:
   a telescoping system of needles comprising:
      (i) an inner guiding needle;
      (ii) at least one tissue separating needle having a distal cutting edge; and
      (iii) an outer needle defining an operating lumen.

19. A method according to claim 18 further comprising removing the consolidated mass using a mechanical cutting instrument.

20. A method according to claim 18 wherein the consolidated mass is removed by destroying the consolidated mass with laser rays and irrigating to remove the destroyed consolidated mass.

21. A method according to claim 18 wherein the consolidated mass is removed by destroying the consolidated mass with high frequency coagulation and irrigating to remove the destroyed consolidated mass.

22. A device for removal of a consolidated mass located within a dense tissue comprising:
   a telescoping system of needles having
      an inner guiding needle;
      one or more concentrically arranged, tissue separating needles surrounding the inner guiding needle; and
      an expandable outer needle defining an operating lumen, wherein an operating lumen diameter increases upon insertion of at least one of the one or more tissue separating needles into the operating lumen.

23. A device according to claim 22, wherein the outer needle includes a longitudinal slit for expansion of the operating lumen.

24. A device according to claim 22, comprising at least two tissue separating needles wherein removal of one of the separating needles provides a gap into which a cannula can be inserted.

25. A device according to claim 22, wherein the device is manufactured from materials selected from the group comprising titanium alloys, nickel alloys, nickel-titanium and stainless steel.

26. A device according to claim 22, wherein a distal end of at least one of the one or more tissue separating needles includes a beveled needle edge that is cone shaped or convex.

27. A device according to claim 22, further comprising a drive motor for distally advancing at least of the one or more tissue separating needles.

28. A device according to claim 27, wherein the drive motor is selected from a group of motors comprising: pneumatic, hydraulic, linear, rotational and piezoelectrical ultrasound motor.

29. A device according to claim 22, wherein at least one of the one or more tissue separating needles is hand driven.

30. A device according to claim 22, further comprising a holding apparatus that comprises:
   a securing arrangement for securing the dense tissue in the holding device in a selected position; and
   a mechanism for advancing at least one of the needles of the telescoping system of needles.

31. A device according to claim 22, further comprising at least two concentrically arranged tissue separating needles, one or more of the at least to concentrically arranged tissue separating needles being removable to leave a gap, and further comprising a cannula sized to fit within the gap.

32. A device according to claim 31, wherein the cannula has a proximal end and a distal end, the distal end including an excising mechanism for excising the consolidated mass, the mechanism including a cutting thread, an arrangement for fixing the cutting thread to the distal of the cannula, and a recess at the distal end of the cannula to receive the thread.

33. A device according to claim 22, wherein the inner guiding needle is a biopsy needle having an outer biopsy needle and an obturator needle, the obturator needle having a notch at a distal end.

34. A device according to claim 22, wherein the inner guiding needle comprises an aspiration needle.

35. A device according to claim 22, wherein inner guiding needle comprises a biopsy device with a rotating cutting edge.

36. A device according to claim 22 wherein a distal end of one of the one or more tissue separating needles and the expandable outer needle include one ore more cutting teeth.

37. A method for removing a consolidated mass from a dense tissue comprising a step of:
   accessing the consolidated mass in the dense tissue by incrementally separating the dense tissue using a telescoping system of needles to create an opening through which the consolidated mass is accessed, the telescoping system of needles comprising an inner guiding needle, one or more concentrically arranged tissue separating needles surrounding the inner guiding needle and an expanding outer needle defining an operating lumen to receive the one or more tissue separating needles; and
   removing the consolidated mass through the opening.

38. A method according to claim 37, wherein removing the consolidated mass includes cutting the consolidated mass from the dense tissue using a mechanical cutting instrument.

39. A method according to claim 37, wherein removing the consolidated mass includes destroying the consolidated mass with laser light and irrigating to remove the destroyed consolidated mass.

40. A method according to claim 37, wherein removing the consolidated mass includes destroying the consolidated mass with high frequency coagulation and irrigating to remove the destroyed consolidated mass.

41. A method according to claim 37, further comprising inserting a tissue separating needle into the expanding out needle so as to increase the diameter of the operating lumen.

42. A method according to claim 37, further comprising expanding an inner diameter of the operating lumen by inserting one or more of the at least two concentrically arranged tissue separating needles into the operating lumen.

* * * * *